(12) United States Patent
Mizutani et al.

(10) Patent No.: US 8,309,700 B2
(45) Date of Patent: Nov. 13, 2012

(54) INHIBITOR OF HISTONE ACETYLTRANSFERASE, ESPECIALLY P300

(75) Inventors: Shuki Mizutani, Chiba (JP); Takayuki Yamada, Kanagawa (JP)

(73) Assignee: Sony Corporation, Tokyo (JP)

(*) Notice: Subject to any disclaimer, the term of this patent is extended or adjusted under 35 U.S.C. 154(b) by 0 days.

(21) Appl. No.: 12/901,382

(22) Filed: Oct. 8, 2010

(65) Prior Publication Data

US 2011/0070653 A1 Mar. 24, 2011

Related U.S. Application Data

(62) Division of application No. 10/490,550, filed as application No. PCT/JP02/08257 on Aug. 13, 2002, now Pat. No. 7,834,169.

(30) Foreign Application Priority Data

Sep. 25, 2001 (JP) ................................. 2001-292206

(51) Int. Cl.
*C07H 21/04* (2006.01)
*C12N 15/00* (2006.01)
(52) U.S. Cl. .................................... 536/23.5; 435/320.1
(58) Field of Classification Search .......................... None
See application file for complete search history.

(56) References Cited

U.S. PATENT DOCUMENTS

| | | | |
|---|---|---|---|
| 6,551,795 B1 | 4/2003 | Rubenfield et al. | |
| 6,783,961 B1 | 8/2004 | Edwards et al. | |
| 6,821,724 B1 | 11/2004 | Mittman et al. | |
| 2005/0048623 A1 | 3/2005 | Hillman et al. | |
| 2008/0145928 A1 | 6/2008 | Mizutani et al. | |

FOREIGN PATENT DOCUMENTS

| | | |
|---|---|---|
| WO | WO 95/30758 | 11/1995 |
| WO | WO 99/14375 | 3/1999 |
| WO | WO 99/58559 | 11/1999 |
| WO | WO 00/58473 | 10/2000 |
| WO | WO 01/07471 | 2/2001 |
| WO | WO 0107471 | * 2/2001 |
| WO | WO 01/60855 | 8/2001 |
| WO | WO 01/64834 | 9/2001 |
| WO | WO 0164834 | * 9/2001 |

OTHER PUBLICATIONS

Zhang et al (Mol Cancer Research, 2009, 7:67-78).*
Guo et al., "Protein Tolerance to Random Amino Acid Change", PNAS vol. 101, (25), pp. 9205-9210 (2004).
Lesk et al., Prediction of Protein Function from Protein Sequence and Structure, pp. 27-28, downloaded Sep. 17, 2007.
Mizutani et al., U.S. Appl. No. 13/296,878, filed Nov. 15, 2011.
Yang et al., "Recruitment of O-GlcNac Transferase to Promoters by Corepressor mSin3A: Coupling O-GlcNacylation to Transcriptional Repression", Cell vol. 110, pp. 69-80 (2002).

Altschul, S. et al., "Basic Local Alignment Search Tool", J. Mol Biol. 215: 403-410 (1990).
Avantaggiati, M.L. et al., "Recruitment of p300/CBP in p53-Dependent Signal Pathways", Cell 89:1175-1184 (1997).
Baniahmad, A. et al., "A transferable silencing domain is present in the thyroid hormone receptor, in the v-erbA oncongene product and in the retinoic acid receptor", EMBO Journal, 11(3), 1015-1023 (1992).
Baudino, T.A. et al., "Isolation and Characterization of a Novel Coactivator Protein, NCoA-62, Involved in Vitamin D-mediated Transcription", J. Biol Chem 273(26), 16434-41 (1998).
Boehringer Mannheim Biochemicals, 1994 Catalog, p. 93.
Borrow, J. et al., "The Translocation t(8;16)(p11;p13) of Acute Myeloid Leukaemia Fuses A Putative Acetyltransferase To The CREB-Binding Protein", Nature Genet., 14:33-41 (1996).
Bowie et al., "Deciphering the Message in Protein Sequences: Tolerance to Amino Acid Substitutions", Science, 247:1306-1310 (1990).
Chaffanet, M. et al., "MOZ Is Fused To p300 In An Acute Monocytic Leukemia With t(8;22)," Genes Chromosomes Cancer, 28:138-144 (2000).
Elbashir, SM. et al., "Duplexes of 21-Nucleotide RNAs Mediate RNA Interference in Cultured Mammalian Cells", Nature, 411: 494-498 (2001).
Fan, S.J. et al., "p53 Gene Mutations Are Associated With Decreased Sensitivity Of Human Lymphoma Cells to DNA Damaging Agents", Cancer Res., 54: 5824-5830 (1994).
Fondell, Joseph D. et al., "Unliganded Thyroid Hormone Receptor Inhibits Formation of a Functional Preinitiation Complex: Implications for Active Repression", Genes & Development 7:1400-1410 (1993).
Fujiwara et al., "Induction of Chemosensitivity In Human Lung Cancer Cells in Vivo By Adenovirus-mediated Transfer of the Wild-Type p53 Gene", Cancer Res., 54, 2287-2291 (1994).
Gayther, S.A. et al., "Mutations Truncating The EP300 Acetylase In Human Cancers", Nature Genet., 24:300-303 (2000).
Hacia, J.G. et al., "Determination of ancestral alleles for human single-nucleotide polymorphisms using high-density oligonucleotide arrays", Nature Genetics (1999)22: 164.
Hirosawa et al., "Characterization of cDNA Clones Selected by the GeneMark Analysis from Size-fractionated cDNA Libraries from Human Brain DNA Research", 6:329-336 (1999).
Ida, K. et al., "Adenoviral E1A-Associated Protein p300 Is Involved In Acute Mayeloid Leukemia With t(11;22)(q23;q13)", Blood, 90:4699-4704 (1997).

(Continued)

*Primary Examiner* — Laura B Goddard
(74) *Attorney, Agent, or Firm* — Finnegan Henderson Farabow Garrett & Dunner L.L.P.

(57) ABSTRACT

An inhibitor of histone acetyltransferase p300 was isolated from human cDNA library and identified as a nuclear protein composed of 855 amino acid residues. It binds to the cysteine/histidine-rich region of p300, thereby inhibiting the transcriptional activation by p300. It also inhibits the transcription activity of p53, with p300 functioning as a coactivator, and inhibits the discontinuance of cell cycle that relies on p53.

5 Claims, 12 Drawing Sheets

OTHER PUBLICATIONS

Karlin and Altschul, "Methods for assessing the statistical significance of molecular sequence features by using general scoring schemes", Proc. Natl. Acad. Sci. USA 87:2264, Mar. 1990.

Karlin and Altschul, "Applications and Statistics for Multiple High-scoring Segments in Molecular Sequences", Proc. Natl. Acad. Sci. Proc. Natl. Acad. Sci. USA 90:5873.

Kitabayashi, I. et al., "Fusion Of MOZ Histone Acetyltransferases in Acute Monocytic Leukemia With A t(8;22)(p11;q13) Chromosome Translocation", Leukemia, 15:89-94 (2001).

Laboratory Manual for Genetic Engineering, 3$^{rd}$ compiled by M. Maturura, issued by Maruzen Co., Ltd. (1996), pp. 242-246.

Lamb, J.R. et al., "Tetratrico peptide repeat interactions: to TPR or not to TPR?," Trends Biochem Sci 20(7), 257-9 (1995).

Lill, N.L. et al. "Binding and Modulation Of p53 By p300/CBP Coactivators", Nature 387:823-827 (1997).

Lowe, S.W. et al. "p53 Status And The Efficacy Of Cancer Therapy In Vivo", Science 266: 807-810 (1994).

Lowe, S.W. et al. "p53-Dependent Apoptosis Modulates The Cytotoxicity Of Anticancer Agents", Cell 74:954-967 (1993).

MacDonald, P.N. et al., "Vitamin D receptor and nuclear receptor coactivators: crucial interactions in vitamin D-mediated transcription", Steroids 66(3-5), 171-6 (2001).

Matsubara, Kenishi and Sakaki, Yosiyuki, "Tactics of SNP Gene Variation", published by Nakayama Shoten, p. 128-135.

Nakatsu et al., "XAB2, A Novel Tetratricopeptide Repeat Protein Involved in Transcription-Coupled DNA Repair and Transcription", J. of Biological Chemistry, 275:34931-34937 (2000).

Niles R.M., "Recent advances in the use of vitamin A (retinoids) in the prevention and treatment of cancer", Nutrition, 16(11-12), 1084-9 (2000).

Niitsu, Y. et al., "Cancer Gene Therapy", Molecular Medicine 35:1385-1395 (1998).

Noda, K. et al., "Gan to kagaku chiryou hou (Cancer and its chemical therapy)", 21, 1633 (1994); "Etoposide 21".

Ogawa, I. et al., "Gan to kagaku chiryou hou (Cancer and its chemical therapy)", 10, 2403 (1983); "VP-16-213 Phase I Study".

Okuno, M. et al., "Retinoids in Liver Fibrosis and Cancer", Front Biosci 7, 204-18 (2002).

Panagopoulos, I. et al., "Fusion Of The MORF and CBP Genes In Acute Myeloid Leukemia With The t(10;16)(q22;p13)," Hum. Mol. Genet., 10:395-404 (2001).

Patel et al., "Production of a Functional Dihydrofolate Synthase with a Cleaveable poly-HisTag in Saccharomyces Cerevisiae",Biotechnology Letters, 24:657-662 (Apr. 2002).

Riecken E.O. and Rosewicz S. "Retinoids in Pancreatic Cancer", Annals of Oncology 10 Suppl 4, 197-200 (1999).

Satake, N. et al., "Novel MLL-CBP Fusion Transcript In Therapy-Related Chronic Myelomonocytic Leukemia With A t(11;16)(q23;p13) Chromosome Translocation", Genes Chromosomes Cancer, 20:60-63 (1997).

Schmutzler C. and Kohrle J., "Retinoic Acid Redifferentiation Therapy for Thyroid Cancer", Thyroid 10(5), 393-406 (2000).

Scolnick, D.M. et al., "CREB-Binding Protein And p300/CBP-Associated Factor Are Transcriptional Coactivators Of The p53 Tumor Suppressor Protein", Cancer Res., 57:3693-3696 (1997).

Seo, S. et al., "Regulation of Histone Acetylation and Transcription by INHAT, a Human Cellular Complex Containing the Set Oncoprotein", Cell, vol. 104, No. 1, pp. 119-130 (Jan. 12, 2001).

Shikama, N. et al., "A Novel Cofactor for p300 That Regulates The p53 Response", Mol. Cell, 4:365-376 (1999).

Smith et al. "The tetratricopeptide repeats of Ssn6 interact with the homeo domain of alpha 2", Genes Dev.9:2903-10. (1995).

Sobulo, O.M. et al., "MLL Is Fused To CBP, A Histone Acetyltransferase, In Therapy-Related Acute Myeloid Leukemia With a t(11;16)(q23;p13.3)," Proc. Natl. Acad. Sci. USA, 94:8732-8737 (1997).

Taki, T. et al., "The t(11;16)(q23;p13) Translocation in Myelodysplastic Syndrome Fuses The MLL Gene To The CBP Gene", Blood, 89:3945-3950 (1997).

Yoshimichi et al., "XAB2, a Novel Tetratricopeptide Repeat Protein Involved in Transcription-coupled DNA Repair and Transcription", Journal Biological Chem., 275:34931-34937 (2000).

Zhang D. et. al., "Retinoids and Ovarian Cancer", J. Cell Physiol 185(1), 1-20, (2000).

Zhang, K. et al., "The *Crooked Neck*Gene of Drosophila Contains a Motif Found in a Family of Yeast Cell Cycle Genes", Genes Dev 5(6), 1080-91 (1991).

Molecular Cloning 3$^{rd}$ Ed, Chapter 2, pp. 2.1.

Molecular Cloning 3$^{rd}$ Ed, Chapter 8, pp. 8.1.

Molecular Cloning 3$^{rd}$ Ed, Chapter 8, Protocol 8, pp. 8.46.

Notification of Reasons for Refusal in Japanese Patent Application No. 2003-530851.

SCORE, Search Results for Application 10490550: See Result 5, pp. 1-14.

Special Coordination Funds for Promoting Science and Technology "Research on Development of Fundamental Technology to Elucidate Genomic Dynamics", (Primary Period: 1996 to 1998), Research Report, Research and Development Bureau, Science and Technology Agency, Sep. 1999.

\* cited by examiner

TPR (TETRATRICOPEPTIDE REPEAT)
ACID REGION

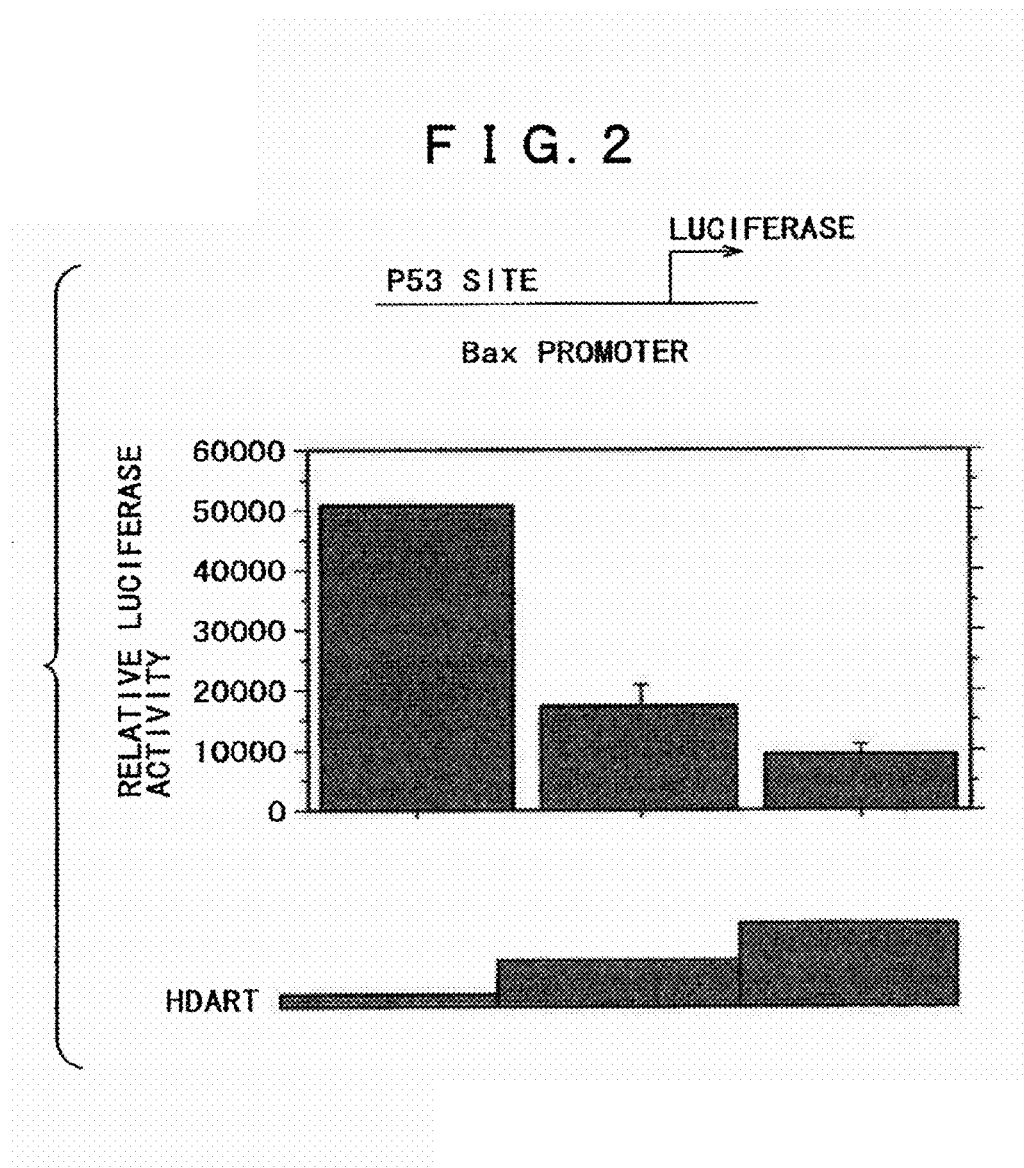

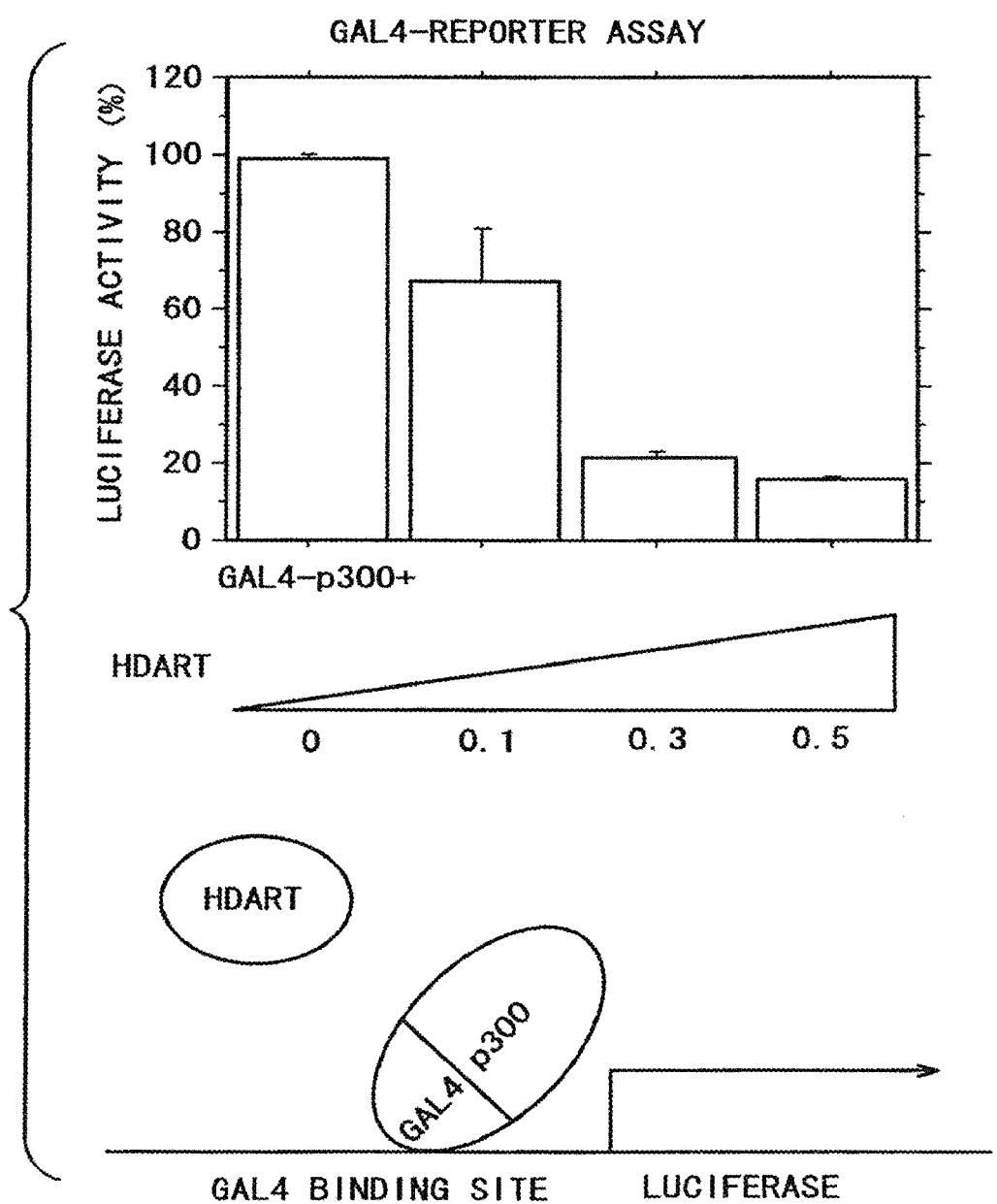

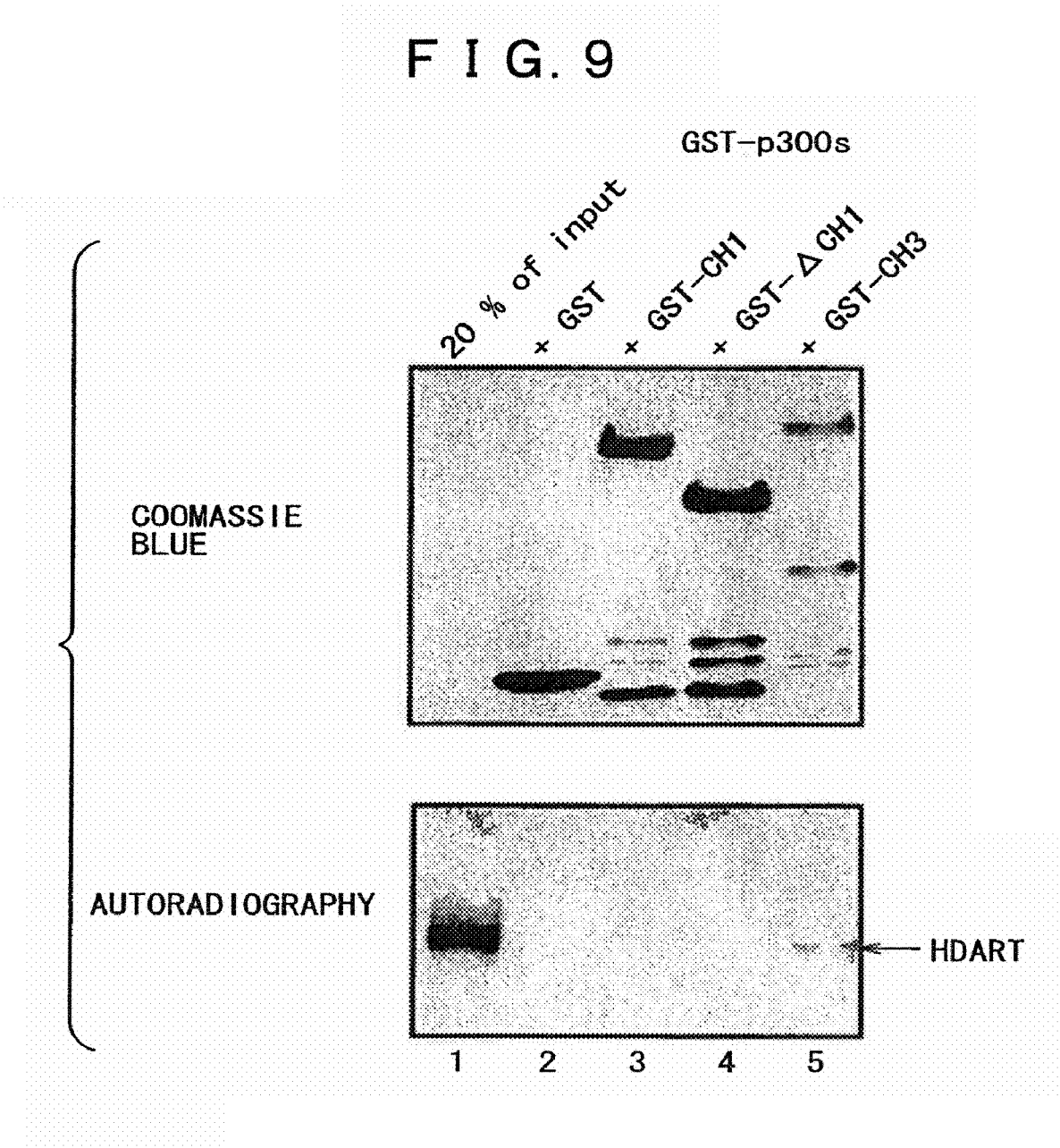

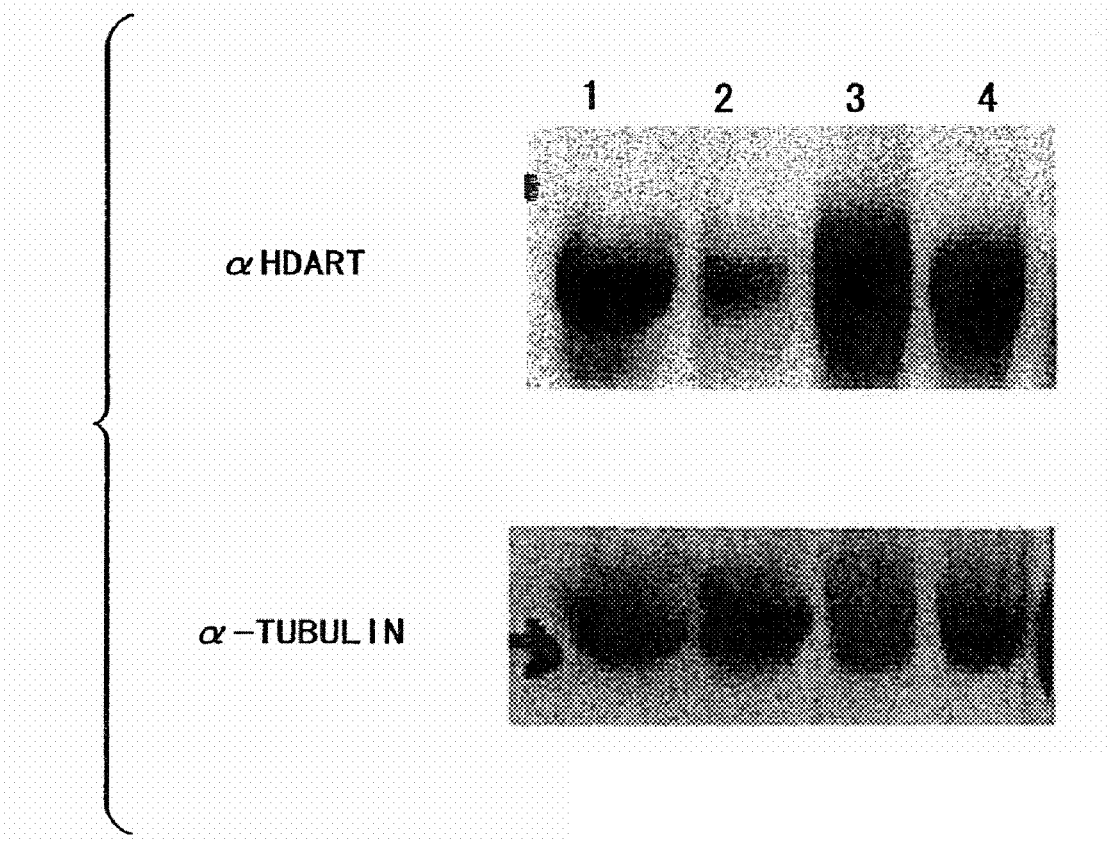

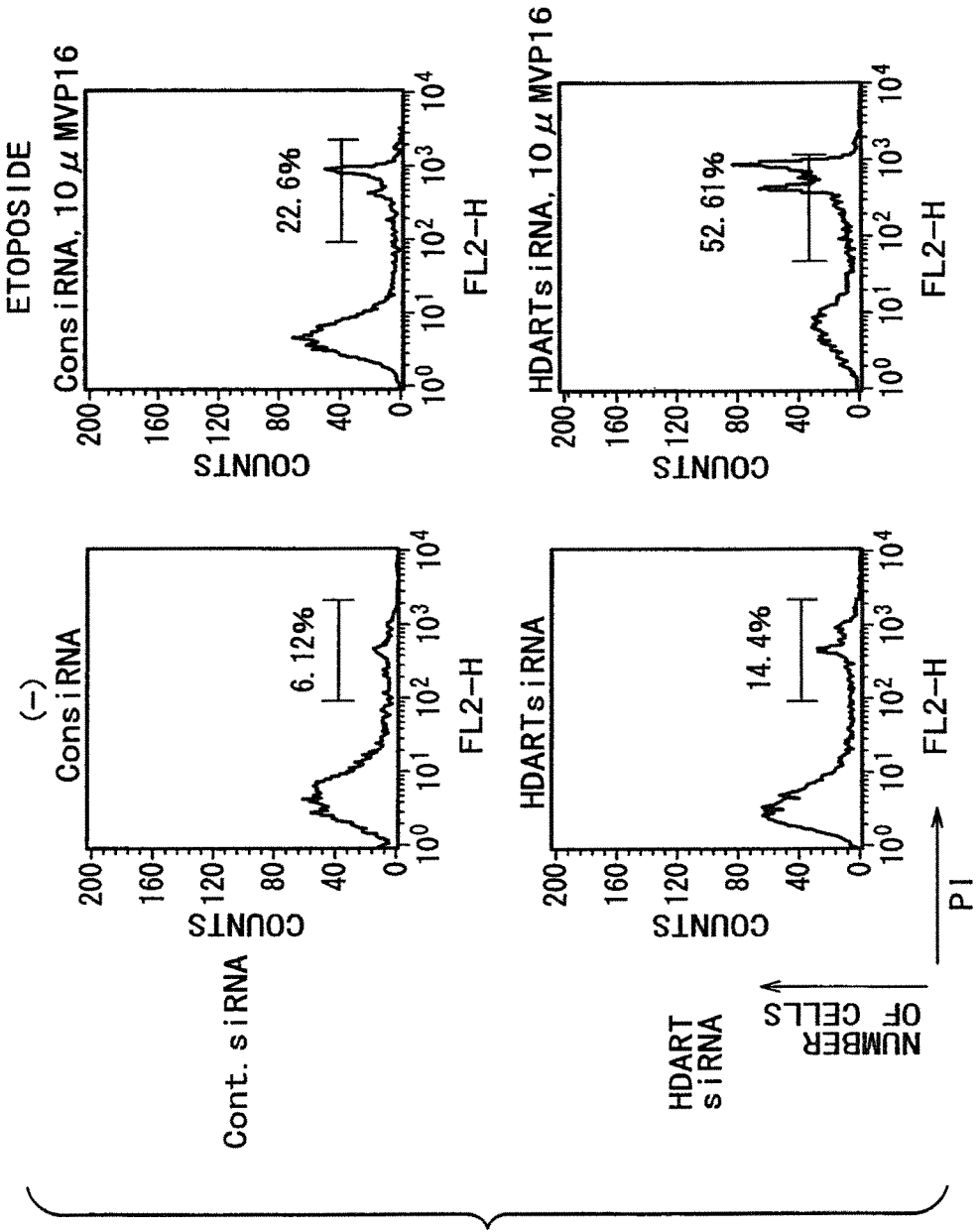

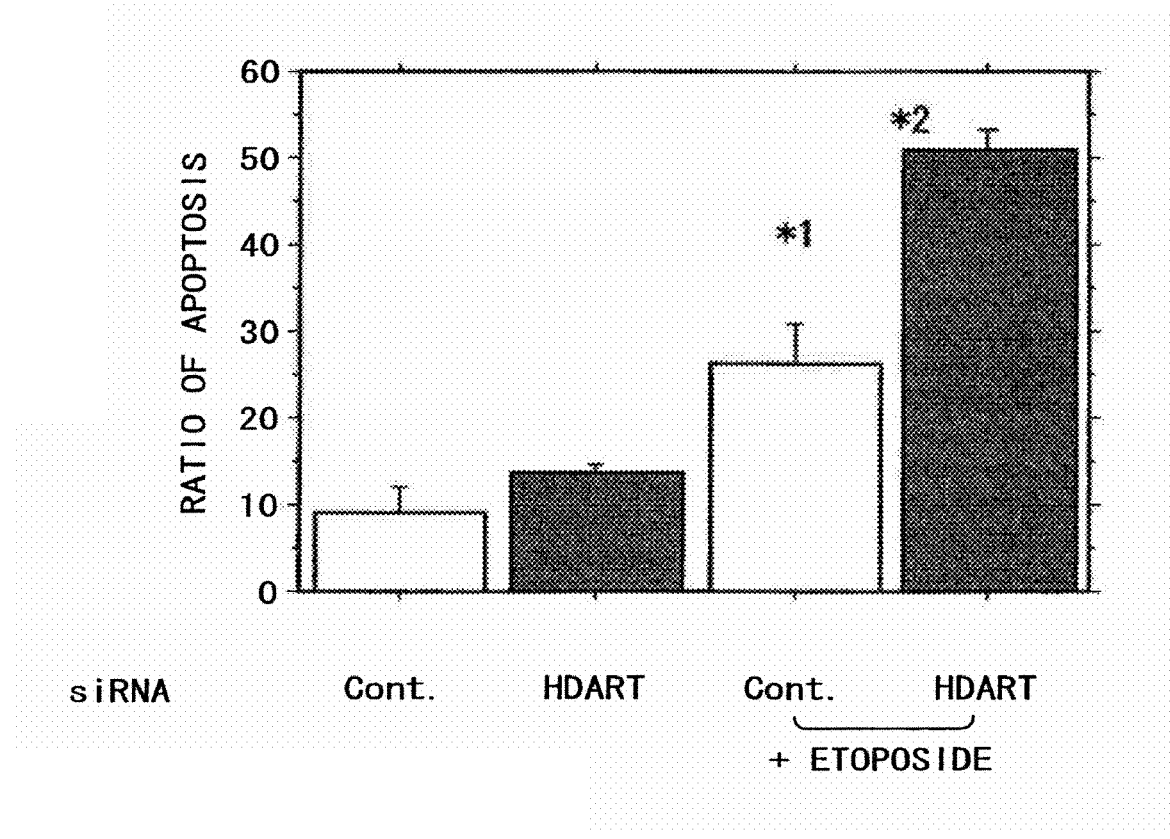

SEQUENCE LISTING

<160> NUMBER OF SEQ ID NOS: 19

<210> SEQ ID NO 1
<211> LENGTH: 2684
<212> TYPE: DNA
<213> ORGANISM: Homo sapiens

<400> SEQUENCE: 1

```
agcgcgcgac tctcctgtac ctgggcatcc agaaaaatgg tggtgatggc gcgactttcg      60
cggcccgagc ggccggacct tgtcttcgag gaagaggacc tcccctatga ggaggaaatc     120
atgcggaacc aattctctgt caaatgctgg cttcgctaca tcgagttcaa acagggcgcc     180
ccgaagccca ggctcaatca gctatacgag cgggcactca agctgctgcc ctgcagctac     240
aaactctggt accgatacct gaaggcgcgt cgggcacagg tgaagcatcg ctgtgtgacc     300
gaccctgcct atgaagatgt caacaactgt catgagaggg cctttgtgtt catgcacaag     360
atgcctcgtc tgtggctaga ttactgccag ttcctcatgg accaggggcg cgtcacacac     420
acccgccgca ccttcgaccg tgccctccgg gcactgccca tcacgcagca ctctcgaatt     480
tggcccctgt atctgcgctt cctgcgctca cacccactgc ctgagacagc tgtgcgaggc     540
tatcggcgct tcctcaagct gagtcctgag agtgcagagg agtacattga gtacctcaag     600
tcaagtgacc ggctggatga ggccgcccag cgcctggcca ccgtggtgaa cgacgagcgt     660
ttcgtgtcta aggccggcaa gtccaactac cagctgtggc acgagctgtg cgacctcatc     720
tcccagaatc cggacaaggt acagtccctc aatgtggacg ccatcatccg cggggcctc     780 acccgcttca ccgaccagct gggcaagctc tggtgttctc tcgccgacta ctacatccgc     840
agcggccatt tcgagaaggc tcgggacgtg tacgaggagg ccatccggac agtgatgacc     900
gtgcgggact tcacacaggt gtttgacagc tacgcccagt tcgaggagag catgatcgct     960
gcaaagatgg agaccgcctc ggagctgggg cgcgaggagg aggatgatgt ggacctggag    1020
ctgcgcctgg cccgcttcga gcagctcatc agccggcggc ccctgctcct caacagcgtc    1080
```

```
ttgctgcgcc aaaacccaca ccacgtgcac gagtggcaca agcgtgtcgc cctgcaccag    1140
ggccgccccc gggagatcat caacacctac acagaggctg tgcagacggt ggaccccttc    1200
aaggccacag gcaagcccca cactctgtgg gtggcgtttg ccaagtttta tgaggacaac    1260
ggacagctgg acgatgcccg tgtcatcctg gagaaggcca ccaaggtgaa cttcaagcag    1320
gtggatgacc tggcaagcgt gtggtgtcag tgcggagagc tggagctccg acacgagaac    1380
tacgatgagg ccttgcggct gctgcgaaag gccacggcgc tgcctgcccg ccgggccgag    1440
tactttgatg gttcagagcc cgtgcagaac cgcgtgtaca agtcactgaa ggtctggtcc    1500
atgctcgccg acctggagga gagcctcggc accttccagt ccaccaaggc cgtgtacgac    1560
cgcatcctgg acctgcgtat cgcaacaccc cagatcgtca tcaactatgc catgttcctg    1620
gaggagcaca agtacttcga ggagagcttc aaggcgtacg agcgcggcat ctcgctgttc    1680
aagtggccca acgtgtccga catctggagc acctacctga ccaaattcat tgcccgctat    1740
gggggccgca agctggagcg ggcacgggac ctgtttgaac aggctctgga cggctgcccc    1800
ccaaaatatg ccaagacctt gtacctgctg tacgcacagc tggaggagga gtggggcctg    1860
gcccggcatg ccatggccgt gtacgagcgt gccaccaggg ccgtggagcc cgcccagcag    1920
tatgacatgt tcaacatcta catcaagcgg gcggccgaga tctatggggt cacccacacc    1980
cgcggcatct accagaaggc cattgaggtg ctgtcggacg agcacgcgcg tgagatgtgc    2040
ctgcggtttg cagacatgga gtgcaagctc ggggagattg accgcgcccg ggccatctac    2100
agcttctgct cccagatctg tgaccccgg acgaccggcg cgttctggca gacgtggaag    2160
gactttgagg tccggcatgg caatgaggac accatcaagg aaatgctgcg tatccggcgc    2220
agcgtgcagg ccacgtacaa cacgcaggtc aacttcatgg cctcgcagat gctcaaggtc    2280
tcgggcagtg ccacgggcac cgtgtctgac ctggcccctg ggcagagtgg catggacgac    2340
atgaagctgc tggaacagcg ggcagagcag ctggcggctg aggcggagcg tgaccagccc    2400
ttgcgcgccc agagcaagat cctgttcgtg aggagtgacg cctcccggga ggagctggca    2460
gagctggcac agcaggtcaa ccccgaggag atccagctgg gcgaggacga ggacgaggac    2520
gagatggacc tggagcccaa cgaggttcgg ctggagcagc agagcgtgcc agccgcagtg    2580
tttgggagcc tgaaggaaga ctgacccgtc cctcccccat ccccccctccc cacccctcc    2640 ccaatacagc tacgtttgta caaaaaaaaa aaaaaaaaaa aaaa              2684
```

<210> SEQ ID NO 2
<211> LENGTH: 855
<212> TYPE: PRT
<213> ORGANISM: Homo sapiens

<400> SEQUENCE: 2

```
Met Val Val Met Ala Arg Leu Ser Arg Pro Glu Arg Pro Asp Leu Val
 1               5                  10                  15

Phe Glu Glu Glu Asp Leu Pro Tyr Glu Glu Ile Met Arg Asn Gln
                20                  25                  30

Phe Ser Val Lys Cys Trp Leu Arg Tyr Ile Glu Phe Lys Gln Gly Ala
            35                  40                  45

Pro Lys Pro Arg Leu Asn Gln Leu Tyr Glu Arg Ala Leu Lys Leu Leu
        50                  55                  60

Pro Cys Ser Tyr Lys Leu Trp Tyr Arg Tyr Leu Lys Ala Arg Arg Ala
    65                  70                  75                  80

Gln Val Lys His Arg Cys Val Thr Asp Pro Ala Tyr Glu Asp Val Asn
                85                  90                  95
```

-continued

```
Asn Cys His Glu Arg Ala Phe Val Phe Met His Lys Met Pro Arg Leu
            100                 105                 110

Trp Leu Asp Tyr Cys Gln Phe Leu Met Asp Gln Gly Arg Val Thr His
            115                 120                 125

Thr Arg Arg Thr Phe Asp Arg Ala Leu Arg Ala Leu Pro Ile Thr Gln
            130                 135                 140

His Ser Arg Ile Trp Pro Leu Tyr Leu Arg Phe Leu Arg Ser His Pro
145                 150                 155                 160

Leu Pro Glu Thr Ala Val Arg Gly Tyr Arg Arg Phe Leu Lys Leu Ser
                165                 170                 175

Pro Glu Ser Ala Glu Glu Tyr Ile Glu Tyr Leu Lys Ser Ser Asp Arg
                180                 185                 190

Leu Asp Glu Ala Ala Gln Arg Leu Ala Thr Val Val Asn Asp Glu Arg
            195                 200                 205

Phe Val Ser Lys Ala Gly Lys Ser Asn Tyr Gln Leu Trp His Glu Leu
            210                 215                 220

Cys Asp Leu Ile Ser Gln Asn Pro Asp Lys Val Gln Ser Leu Asn Val
225                 230                 235                 240

Asp Ala Ile Ile Arg Gly Gly Leu Thr Arg Phe Thr Asp Gln Leu Gly
                245                 250                 255

Lys Leu Trp Cys Ser Leu Ala Asp Tyr Tyr Ile Arg Ser Gly His Phe
            260                 265                 270

Glu Lys Ala Arg Asp Val Tyr Glu Glu Ala Ile Arg Thr Val Met Thr
            275                 280                 285

Val Arg Asp Phe Thr Gln Val Phe Asp Ser Tyr Ala Gln Phe Glu Glu
            290                 295                 300

Ser Met Ile Ala Ala Lys Met Glu Thr Ala Ser Glu Leu Gly Arg Glu
305                 310                 315                 320

Glu Glu Asp Asp Val Asp Leu Glu Leu Arg Leu Ala Arg Phe Glu Gln
                325                 330                 335

Leu Ile Ser Arg Arg Pro Leu Leu Leu Asn Ser Val Leu Leu Arg Gln
            340                 345                 350

Asn Pro His His Val His Glu Trp His Lys Arg Val Ala Leu His Gln
            355                 360                 365

Gly Arg Pro Arg Glu Ile Ile Asn Thr Tyr Thr Glu Ala Val Gln Thr
370                 375                 380

Val Asp Pro Phe Lys Ala Thr Gly Lys Pro His Thr Leu Trp Val Ala
385                 390                 395                 400

Phe Ala Lys Phe Tyr Glu Asp Asn Gly Gln Leu Asp Asp Ala Arg Val
                405                 410                 415

Ile Leu Glu Lys Ala Thr Lys Val Asn Phe Lys Gln Val Asp Asp Leu
            420                 425                 430

Ala Ser Val Trp Cys Gln Cys Gly Glu Leu Glu Leu Arg His Glu Asn
            435                 440                 445

Tyr Asp Glu Ala Leu Arg Leu Leu Arg Lys Ala Thr Ala Leu Pro Ala
450                 455                 460

Arg Arg Ala Glu Tyr Phe Asp Gly Ser Glu Pro Val Gln Asn Arg Val
465                 470                 475                 480

Tyr Lys Ser Leu Lys Val Trp Ser Met Leu Ala Asp Leu Glu Glu Ser
                485                 490                 495

Leu Gly Thr Phe Gln Ser Thr Lys Ala Val Tyr Asp Arg Ile Leu Asp
            500                 505                 510

Leu Arg Ile Ala Thr Pro Gln Ile Val Ile Asn Tyr Ala Met Phe Leu
```

```
                      515                 520                 525
Glu Glu His Lys Tyr Phe Glu Glu Ser Phe Lys Ala Tyr Glu Arg Gly
            530                 535                 540
Ile Ser Leu Phe Lys Trp Pro Asn Val Ser Asp Ile Trp Ser Thr Tyr
545                 550                 555                 560
Leu Thr Lys Phe Ile Ala Arg Tyr Gly Gly Arg Lys Leu Glu Arg Ala
                565                 570                 575
Arg Asp Leu Phe Glu Gln Ala Leu Asp Gly Cys Pro Pro Lys Tyr Ala
            580                 585                 590
Lys Thr Leu Tyr Leu Leu Tyr Ala Gln Leu Glu Glu Glu Trp Gly Leu
            595                 600                 605
Ala Arg His Ala Met Ala Val Tyr Glu Arg Ala Thr Arg Ala Val Glu
            610                 615                 620
Pro Ala Gln Gln Tyr Asp Met Phe Asn Ile Tyr Ile Lys Arg Ala Ala
625                 630                 635                 640
Glu Ile Tyr Gly Val Thr His Thr Arg Gly Ile Tyr Gln Lys Ala Ile
                645                 650                 655
Glu Val Leu Ser Asp Glu His Ala Arg Glu Met Cys Leu Arg Phe Ala
            660                 665                 670
Asp Met Glu Cys Lys Leu Gly Glu Ile Asp Arg Ala Arg Ala Ile Tyr
            675                 680                 685
Ser Phe Cys Ser Gln Ile Cys Asp Pro Arg Thr Thr Gly Ala Phe Trp
            690                 695                 700
Gln Thr Trp Lys Asp Phe Glu Val Arg His Gly Asn Glu Asp Thr Ile
705                 710                 715                 720
Lys Glu Met Leu Arg Ile Arg Arg Ser Val Gln Ala Thr Tyr Asn Thr
                725                 730                 735
Gln Val Asn Phe Met Ala Ser Gln Met Leu Lys Val Ser Gly Ser Ala
            740                 745                 750
Thr Gly Thr Val Ser Asp Leu Ala Pro Gly Ser Gly Met Asp Asp
            755                 760                 765
Met Lys Leu Leu Glu Gln Arg Ala Glu Gln Leu Ala Ala Glu Ala Glu
            770                 775                 780
Arg Asp Gln Pro Leu Arg Ala Gln Ser Lys Ile Leu Phe Val Arg Ser
785                 790                 795                 800
Asp Ala Ser Arg Glu Glu Leu Ala Glu Leu Ala Gln Gln Val Asn Pro
                805                 810                 815
Glu Glu Ile Gln Leu Gly Glu Asp Glu Asp Glu Met Asp Leu
            820                 825                 830
Glu Pro Asn Glu Val Arg Leu Glu Gln Gln Ser Val Pro Ala Ala Val
            835                 840                 845
Phe Gly Ser Leu Lys Glu Asp
850                 855

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgatgtagcg aagccagcat ttgac                                          25

<210> SEQ ID NO 4
```

```
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtcgcgccat caccaccatt tttctg                                          26

<210> SEQ ID NO 5
<211> LENGTH: 30
<212> TYPE: DNA
<213> ORGANISM: Artificial Sequence
<220> FEATURE:
<223> OTHER INFORMATION: Synthetic
      primer

<400> SEQUENCE: 5
caggatccgt ttgaacacta cgcccagttc                                      30

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gttctcgagg tcatccacct gcttgagg                                        28

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggaagcttcc tgccgaagtc agttccttgt gga                                  33

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccaagcttcc tgtgggcgga ttagggctt                                       29

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atggataagg tgggggatgc                                                 20

<210> SEQ ID NO 10
<211> LENGTH: 20
<212> TYPE: DNA
```

-continued

<213> ORGANISM: Artificial Sequence
<220> FEATURE:
<223> OTHER INFORMATION: Description of Artificial Sequence: Synthetic
      primer

<400> SEQUENCE: 10
tgatccatgt agcgactttc                                               20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gacctgacag actacctcat                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agacagcact gtgttggcat                                               20

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctggatccgg aattcatggt ggtgatggcg cgac                               34

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggatccacgg gtcagtcttc cttcag                                        26

<210> SEQ ID NO 15
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 15
aaccaattct ctgtcaaatg c                                             21

<210> SEQ ID NO 16
<211> LENGTH: 21

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 16
ccaauucucu gucaaaugct t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 17
gcauuugaca gagaauuggt t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 18
cuuacgcuga guacuucgat t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 19
ucgaaguacu cagcguaagt t                                              21
```

INHIBITOR OF HISTONE ACETYLTRANSFERASE, ESPECIALLY P300

This is a division of application Ser. No. 10/490,550, 35 U.S.C. §371(c) date Nov. 1, 2004, now U.S. Pat. No. 7,834,169 which is a national stage entry of International Patent Application No. PCT/JP02/08257, filed Aug. 13, 2002, which claims the benefit of Japanese Patent Application No. 2001-292206, filed Sep. 25, 2001, all of which are incorporated herein by reference.

TECHNICAL FIELD

The present invention relates to an inhibitor of histone acetyltransferase, especially p300.

BACKGROUND ART p53 is widely known to have characteristic properties as follows. It is expressed and induced in response to stress etc. causing genetic toxicity. It activates the transcription of various genes. It brings about bioactivity such as cell cycle arrest, DNA repair, and apoptosis induction. The resent investigation on p53 revealed that the activation of transcription by p53 involves a histone acetyltransferase as the transcription coupling factor. The histone acetyltransferase acetylates the ε-amino group of the specific Lys residue in the histone N-terminus domain, thereby neutralizing positive charges. It is considered that acetylation of histone relaxes the nucleosome structure, thereby making the transcription factor to be recruited easily, which leads to the activated transcription. The histone acetyltransferase involving the activation of transcription by p53 is known to include p300, PCAF, PML, MOZ, etc. It has been reported that p300 acetylates p53 as well as histone, thereby enhancing the ability of p53 to bind to a specific DNA. (Avantaggiati M L. et al., Cell 89:1175-1184 (1997), Lill N L. et al., Nature 387:823-827 (1997)) It has turned out that p300 have CH1 and CH3 domains rich in cysteine/histidine and Q-rich domain rich in glutamine and any one of these domains binds to the N-terminal transcription activating domain.

It has also been reported that PCAF, in conjunction with p300, functions as the coactivator of p53. (Scolnick, D. M. et al., Cancer Res., 57:3693-3696 (1997)) JMY, in conjunction with p300, functions as the coactivator of p53, thereby activating Bax gene which induces apoptosis. (Shinkama, N. et al., Mol. Cell, 4:365-376 (1999)) As mentioned above, it has turned that p300 is a coupling factor essential for p53 to express its function. It has also turned out that p300 functions not only as the transcription coactivator for p53 but also as the coactivator of various transcription factors, such as p73 (p53 family), CREB, AML1; Myb, NF-κB, STAT, C/EBP, IRF3, and MyoD.

On the other hand, just as mutation of p53 gene is observed in a cancer patient, so mutation of p300 is observed in a cancer patient. The shedding of p300 gene due to translocation of chromosome is observed in a patient of acute myelogenous leukemia. (Kitabayashi, I. et al., Leukemia, 15:89-94 (2001), Chaffanet, M. et al., Genes Chromosomes Cancer, 28:138-144 (2000), Ida, K. et al., Blood, 90:4699-4704 (1997), Satake, N. et al., Genes Chromosomes Cancer, 20:60-63 (1997), Taki, T. et al., Blood, 89:3945-3950 (1997), Sobulo, O. M. et al., Proc. Natl. Acad. Sci. USA, 94:8732-8737 (1997), Borrow, J. et al., Nature Genet., 14:33-41 (1996), Panagopoulos, I. et al., Hum. Mol. Genet., 10:395-404 (2001)) There is another report concerning mutation of p300 gene in solid cancer such as large bowel cancer and breast cancer. (Gayther, S. A. et al., Nature Genet., 24:300-303 (2000)) Moreover, p300 is a target of oncogene product of an oncogenic virus. Adenovirus E1A, SV40T antigen, papilloma virus E6, and Tax of HTLV bind to p300 to inhibit its function. It is conjectured that the mutation of p300 gene and the binding of p300 to oncogene product prevent p53 as a coactivator from activating transcription for p300 and this is the cause of transformation.

As mentioned above, the histone acetyltransferase p300 plays an important role for p53 to express bioactivity. It has been suggested that transformation would be induced if the function of p300 is inhibited. Therefore, development of an inhibitor will be useful for analyzing the function and action of p300. It is also expected that it will be useful for elucidation of transformation involving p300 if it is known whether or not there exists p300 inhibitor in a living organism although mutation of p300 gene has been observed in cancer patients.

DISCLOSURE OF INVENTION

It is an object of the present invention to provide a method for identifying human-derived p300 inhibitor which will be useful for analysis of transcription or diseases involving p300. It is another object of the present invention to provide the p300 inhibitor, a nucleic acid coded therewith, and a specific antibody.

The present inventors found from the human cDNA library that there exists a gene product which binds to p300, thereby inhibiting the activation of transcription by p300, and they isolated and identified that gene. In addition, the present inventors showed that the activity of p53 is actually inhibited by expression of HDART. Moreover, the present inventors investigated to see how the physiological function of p53 is affected if the expression of intrinsic HDART is inhibited, and they proved that inhibited expression of HDART causes p53 to strongly express its function.

Furthermore, the present inventors developed an antibody for the inhibitor and a method for screening an inhibiting substance for the inhibitor. The present invention resides in what follows.

(1) A nucleic acid coded with a p300 inhibitor defined in (A) or (B) below.
(A) An inhibitor having the amino acid sequence listed in sequence No. 2.
(B) An inhibitor having the amino acid sequence listed in sequence No. 2, in which one or more amino acids substituted, deleted, inserted, and/or added.
(2) A nucleic acid defined in (A) or (B) below which is coded with a p300 inhibitor.
(A) DNA containing the code region of the base sequence listed in sequence No. 1.
(B) A nucleic acid that hybridizes with DNA having the base sequence listed in sequence No. 1.
(3) A nucleic acid having the base sequence listed in sequence No. 1 or a nucleic acid which is complementary to the complementary strand and has a length of at least 15 nucleotides.
(4) A p300 inhibitor coded with the nucleic acid defined in (1) or (2) above.
(5) An antibody specific for the p300 inhibitor defined in (4) above.
(6) A composition for inhibition of transcription which contains the p300 inhibitor defined in (4) above or a nucleic acid coded with the inhibitor defined in (1) or (2) above.
(7) A method for screening an inhibiting substance that inhibits the p300 inhibitor defined in (4) above, the method including a step of bringing a test sample into contact with the p300 inhibitor defined in (4) above, a step of detecting avidity between the p300 inhibitor and the test sample, and a step of selecting a compound possessing the avidity.

(8) A method for screening an inhibiting substance that inhibits the p300 inhibitor defined in (4) above, the method including a step of bringing p300 into contact with the p300 inhibitor defined in (4) above in the presence of a test sample, a step of measuring avidity between the p300 inhibitor and the p300, and a step of selecting a compound that makes avidity between the p300 inhibitor and the p300 lower than avidity between the p300 inhibitor and the p300 in the absence of a test sample.

The invention will be described in more detail with reference to its embodiments.

The present invention relates to a p300 inhibitor. (In this specification, the p300 inhibitor is referred to as HDART.) Here, "p300" denotes a nuclear phosphoprotein composed of 2414 amino acids which was identified in humans; however, it also includes any protein homologous to it so long as HDART binds to it to inhibits its function. An example of the homologous protein is CBP, which is a nuclear phosphoprotein composed of 2441 amino acids (and hence is approximately equal in length to p300 mentioned above). Both of them have three CH regions rich in cysteine and histidine, (designated as CH1, CH2, and CH3 from the N-terminus) and also have a bromodomain (Br) between CH1 and CH2. They also have a glutamine-rich (Q-rich) region at the C-terminus. They show very high homology in these functional domains. (To be concrete, 93% in CH1 region, 95% in the central 800 amino acids, and 60% as a whole.) The present inventors demonstrated in their experiments on the binding of p300 and HDART that HDART binds to the CH1 region of p300. Thus, in this specification, "p300" includes "CBP" as a protein homologous or analogous thereto so long as HDART binds to CBP having high homology to p300 in CH1 region to inhibit its functions.

The p300 mentioned above functions as a coactivator for transcription factors, such as p53, p73 (p53 family), CREB, AML1, Myb, NF-κB, STAT, C/EBP, IRF3, and MyoD. Therefore, the p300 inhibitor also functions as an inhibitor for these transcription factors with which it couples, by inhibition of the function of p300. An example of the p300 inhibitor is HDART having the amino acid sequence listed in the sequence No. 2. Another example equivalent to HDART is an HDART-analogous protein which, like HDART, binds to p300 to inhibit its functions. Such a protein is included in "p300 inhibitor (or HDART)" in this specification. Example of the analogous protein include those proteins having the amino acid sequence listed in sequence No. 2 with one or more amino acids substituted, deleted, inserted, and/or added.

The HDART-analogous proteins include variants of HDART proteins isolated from humans, HDART counterparts isolated from other organisms, and artificially created HDART variants. Incidentally, in this specification, the term "isolate" is used to mean a substance (such as polynucleotide and polypeptide) which has been extracted from the original environment (which may be the natural environment if it occurs naturally) and then modified by man from its natural state. Moreover, the term "isolate" is used to mean a compound present in the sample which is rich substantially with the subject compound and/or to mean a compound present in the sample in which the subject compound is partially or substantially purified. The term "substantially purified" is used to mean a compound (such as polynucleotide and polypeptide) which has been separated from the natural environment and which excludes other natural components more than 60%, preferably more than 75%, and most desirably more than 90%.

"The amino acid sequence some amino acids substituted, deleted, inserted, and/or added" is not specifically restricted in the number and position of mutation of amino acids so long as the HDART protein retains its function. The number of mutation in all amino acids should typically be less than 10%, preferably be less than 5%, and more preferably less than 1%.

Being a human-derived nuclear protein, HDART can be prepared by extraction of human nuclear protein, followed by purification with the help of an antibody against HDART. Purification may also be accomplished in a simple way with the help of a transformant having a vector which supports DNA coded with HDART which is listed in sequence No. 1, which will be mentioned later.

Preparation of a protein similar to HDART mentioned above may be accomplished by using the technique of hybridization which is known to those skilled in the art. The procedure for preparation may consist of isolating DNA which is highly homologous to cDNA of HDART by hybridization from mammals including humans and other various species. The thus isolated DNA yields the desired protein similar to HDART. Hybridization is accomplished by using as a probe the base sequence of DNA coded with HDART or the base sequence or part thereof listed in sequence No. 1. Preparation may also be accomplished by the well-known technique of PCR (polymerase chain reaction) which employs as a primer the base sequence (or part thereof) listed in sequence No. 1.

It is easy for those skilled in the art to select stringent conditions for hybridization to isolate DNA coded with a protein which is functionally equivalent to the HDART protein. An example of the procedure for hybridization is shown below. First, a hybridization solution is prepared from 25% formamide or 50% formamide under more stringent conditions, 4×SSC, 50 mM HEPES pH 7.0, 10×Denhardt's solution, and 20 μg/ml of denatured salmon sperm DNA. Prehybridization is carried out overnight at 42° C. in this solution. With a labeled probe added, the solution is kept overnight at 42° C. for hybridization. The procedure is completed by cleaning with 1×SSC and 0.1% SDS at 37° C., or with 0.5× SSC and 0.1% SDS at 42° C. under stringent conditions, or with 0.2×SSC and 0.1% SDS at 65° C. under more stringent conditions. The more stringent is the cleaning conditions for hybridization, the more likely it is to isolate DNA highly homologous to the probe sequence. The above-mentioned combination of conditions for reagents such as SSC and SDS and temperature is merely exemplary; the desired stringency for hybridization may be achieved by those skilled in the art if the above-mentioned factors and other factors (such are probe concentration, probe length, and reaction time for hybridization) are adequately combined.

The polypeptide to be coded with the DNA isolated by the technique of hybridization mentioned above is highly homologous in amino acid sequence to the polypeptide which has been identified by present inventors. The high homology means homology in sequence more than 40%, preferably more than 60%, more preferably more than 80%, more preferably more than 90%, more preferably more than 95%, and more preferably more than 97% (e.g., from 98% to 99%). The identity of amino acid sequence may be determined by the algorithm BLAST developed by Karlin and Altschul (Proc. Natl. Acad. Sci. USA 87:2264-2268, 1990, and Proc. Natl. Acad. Sci. USA 90:5873-5877, 1993). This algorithm has developed into a new program called BLASTX. (Altschul et al., J. Mol. Biol. 215:403-410, 1990) Parameters for analysis of amino acid sequence by BLASTX should be such that score=50 and wordlength=3. Parameters for BLAST and Gapped BLAST program used in combination should be the default parameters of each program. The practical method for analysis is known.

The protein analogous to HDART is not limited to the one isolated from the natural world, but it may be prepared by artificial modification from the HDART protein composed of amino acids listed in sequence No. 2. This artificial modification may be performed on the DNA coded with the HDART protein such as the one listed in sequence No. 1 by the technique known to those skilled in the art, the method for producing deletion-mutant, the PCR method, and site-directed mutagenesis with cassette mutation.

Whether or not the thus obtained protein analogous to HDART binds to p300 to inhibit its function as HDART does may be judged by measuring its avidity to p300 with the help of Two hybrid system or immunoprecipitation or by measuring the activity of p300 to inhibit transcription as demonstrated in Example 8.

The HDART protein and any protein analogous thereto inhibit the function of promoting transcription by transcription factor which is produced by p300 as a coactivator of transcription factor. Therefore, these proteins are useful as an experimental tool to analyze the transcription factors in which p300 is involved. They are also useful for development of new drugs to suppress the abnormal apoptosis that occurs when the functions of p300 and p53 are enhanced.

The present invention relates also to DNA coded with p300 inhibitor. The DNA coded with p300 inhibitor includes DNA coded with HDART and DNA coded with HDART-analogous protein.

An adequate example of HDART-coded DNA is the coding region listed in sequence No. 1. Also, the DNA coded with an analogous protein can be sorted from the cDNA library derived from the biological tissue in which the protein having the p300 avidity is expressed, by means of hybridization that employs a probe labeled with DNA or a fragment thereof listed in sequence No. 1. Alternatively, it may also be obtained by means of RT-PCR that employs as a template the total RNA derived from the tissue in which the protein having the above-mentioned avidity is expressed, with the primer being a synthetic nucleotide containing a part of DNA listed in sequence No. 1.

The above-mentioned DNA may also be synthesized by using a commercial DNA synthesizer. A typical process consists of synthesis DNA and complementary strand thereof listed in sequence No. 1 and subsequent annealing for conversion into a double strand.

The above-mentioned DNA may be used to produce p300 inhibitor and also to cause the p300 inhibitor to express in vivo, thereby analyzing the function of p300. In these cases, the DNA may be connected to an adequate expression vector, which may be properly selected by means of translation used for production of proteins. Translation may be that of either cell system or cell-free system, which is properly selected according to the object. In the cell system, it is possible to use pGEX5X-1 (Amersham), pTrcHis (Invitrogen), or the like as the vector to be expressed by *Escherichia coli*. These expression vectors are expressed as fusion protein with other proteins (such as glutathione-S-tranferase and histidine tag). This facilitates purification of proteins mentioned later. It is also possible to use Baculovirus in production of proteins with the help of insect cells or mammalian cells. (Laboratory Manual for Genetic Engineering, 3rd complied by M. Matumura, issued by Maruzen Co., Ltd. (1996) pp. 242-246)

Recombinant proteins which have been expressed in host cells can be purified by any known process. Also, in the case where the proteins specified in the present invention are expressed in the form of fusion protein with glutathione-S-tranferase (GST) or histidine tag as mentioned above, it is possible to purify them by means of glutathione Sepharose column or nickel column or the like.

The HDART-coded DNA mentioned above may be applied to remedy of diseases resulting from mutation or deletion of HDART gene or diseases involving apoptosis due to abnormal enhancement of p300. For this purpose, it should preferably be incorporated into a vector that carries it to the desired tissue or cell. Examples of the vector for gene therapy include retrovirus vector, adenovirus vector, adeno-associated virus vector, vacciniavirus vector, lentivirus vector, herpesvirus vector, alphavirus vector, EB virus vector, papillomavirus vector, and formyvirus vector. Additional examples include non-virus vectors such as cationic ribosome, ligand-DNA complex, and gene gun. (Y. Niitus et al., Molecular Medicine 35:1385-1395 (1998) Introduction of gene may be accomplished in vivo or ex vivo.

The above-mentioned DNA does not necessarily need to be used in its complete form. Its fragment may be used as a probe for hybridization, a PCR primer, or a ribozyme derivative. A fragment of the DNA used for this purpose should preferably have a length of at least 15 nucleotides enough for it to retain the specificity as a probe. An example of such polynucleotides is one which is hybridized specifically with DNA or complementary strand thereof of base sequence listed in sequence No. 1. Here, "Hybridized specifically" means that hybridization takes place such that cross-hybridization with DNA coded with other proteins does not have significance. The above-mentioned probe and primer may be used for cloning of DNA coded with HDART or analogous protein or for analysis of functions of HDART. They may also be used for detection of polymorphism and mutation of HDART gene or cDNA by restriction fragment polymorphism analysis. They may also be used for diagnosis of diseases resulting from p300 inhibition by HDART.

The present invention relates also to an antibody which binds to p300 inhibitor protein. This antibody may be either polyclonal antibody or monoclonal antibody so long as it specifically recognizes and binds to the protein of the present invention. The polyclonal antibody may be obtained by immunizing an animal such as rabbit and guinea pig with the protein of the present invention or partial peptide thereof by the well-known method and subsequently collecting serum from peripheral blood of the immunized animal after confirming an increase in antibody titer. On the other hand, the monoclonal antibody may be obtained by the steps of immunizing an animal such as mouse with the protein of the present invention or partial peptide thereof by the well-known method, collecting spleen or lymph node of the immunized animal after confirming an increase in antibody titer, fusing antibody-forming cells in these tissues with myeloma cells, thereby giving hybridomas, and recovering the antibody produced by the hybridomas from the culture supernatant.

These antibodies may be used when the inhibitor of the present invention undergoes affinity purification. They may also be used, by detecting the amount of expression of the protein of the present invention, for examination and diagnosis of diseases resulting from expression anomaly or structure anomaly of HDART in the test subject. In the case where these antibodies are used to detect the inhibitor of the present invention, it is possible to employ such techniques as ELISA, RIA, and western blotting.

The present invention relates also to a method for screening the HDART inhibitor that inhibits HDART. The first embodiment of the screening method consists of a step of bringing a test sample into contact with HDART, a step of detecting avidity between the HDART and the test sample, and a step of selecting a compound which possesses the avidity.

To be concrete, the first embodiment of the screening method is accomplished in the following manner. First, a test sample which is expected to contain a compound to combine with HDART is brought into contact with HDART. Such a test sample is a cell culture supernatant or a cell extract. Then, the antibody of the present invention is added, so that the compound immunoprecipitates together with HDART. The candidate compound contained in the product of immunoprecipitation can be detected by electrophoresis. The candidate compound can be recovered from the sample in which binding has been detected, by using binding with HDART, for example, by using affinity chromatography.

A typical means to practice the screening method is "western blot technique". This technique consists of the following steps. First, a cDNA library is prepared by using phase vector from a tissue or cell in which expression of a protein that combines with HDART is expected. Then, it is made to express on agarose and transferred to a filter. It is reacted with labeled HDART, and plaques that express the binding protein are detected. The above-mentioned screening may also be accomplished by using "TWO hybrid system" as follows. A fusion protein of GAL4 DNA binding region (DNA-BD) and the HDART is prepared. A library fusion body of GAL4 transcription activating region (AD) and the sample nucleic acid (or sample cDNA) is prepared. Both of them are made to express in yeast. If they react with each other, DNA-BD and AD come close to each other, with the reporter gene expressing. Expression of the reporter gene is used as an index to select yeast containing the candidate compound. From the cells of the selected yeas is recovered the library fusion body. In this way it is possible to obtain the substance which reacts with HDART.

It is also possible to obtain the desired compound by reacting HDART immobilized on a solid phase with a synthetic compound, natural bank, or random phage peptide display library and then screening the molecules that have bound to it. There is another method of isolating the candidate compound by high throughput screening which is based on the combinatorial chemistry technology. These methods are known to those who are skilled in the art.

The second embodiment of the method for screening the HDART inhibitor consists of a step of bringing p300 into contact with HDART in the presence of a test sample, a step of determining avidity between the HDART and the p300, and a step of selecting a compound which lowers the avidity between the HDART and the p300 below the avidity between the HDART and the p300 in the absence of a test sample. In other words, this method is able to select not only a compound which binds to HDART and inhibits binding to p300 but also a compound which binds to p300 and inhibits binding to HDART, thereby preventing p300 inhibiting activity by HDART.

The second embodiment of the screening method may be an immunological one such as immunoprecipitation mentioned above. Such a screening method is accomplished as follows. First, a sample which is expected to contain a compound to combine with HDART is mixed with p300 and HDART. The sample in this case may be a cell culture supernatant or a cell extract. After immunoprecipitation with an anti HDART antibody or an anti p300 antibody, the desired HDART inhibiting substance can be selected by knowing that the amount of p300 or HDART in the product of immunoprecipitation without a test sample is lower than that with a test sample.

Screening can also be accomplished by using the property that p300 combines with the promoter of Bax gene through p53, thereby promoting transcription, and HDART suppresses transcription by p53 and p300. In this case, the reporter gene is connected to the downstream of Bax promoter, and p300, HDART, and a test sample are applied in the presence of p53. The compound which has increased the expression of the reporter gene more than that in the case where only p300 and HDART are applied can be selected. Incidentally, the Bax promoter is an example of the promoters which cause p300 to promote transcription through coupling with the transcription factor. Other techniques for screening by conversion into promoter associated with p300 are known to those skilled in the art. The reporter gene mentioned above is not specifically restricted so long as its expression can be detected. It includes luciferase, CAT gene, $\beta$-galactosidase gene or the like which are generally used for analyses by those skilled in the art.

Incidentally, the test samples suitable for the above-mentioned screening method include, for example, cell extract, expression product of gene library, synthetic low-molecular weight compounds, proteins, natural or synthetic polypeptides, natural compounds, and serum. The are merely exemplary. The test sample may also be any compound isolated by screening by reference to avidity with the protein of the present invention.

The compound selected by the screening method may be used to promote transcription from various transcription factor by p300 through HDART inhibition, thereby making transcription factors such as p53 express bioactivity. Consequently, in the case where p300 has its function inhibited by HDART anomaly, it is possible to control the expression of HDART with the selected compound.

BRIEF DESCRIPTION OF DRAWINGS

FIG. 1A schematically shows the structure of HDART protein. Hatched boxes represent tetratricopeptide repeat (sequence consisting of 34 amino acids) and black boxes represent acid regions. FIG. 1B shows the result of intracellular local analysis of HDART and indicates that HDART is a nuclear protein.

FIG. 2 is a graphical representation showing that HDART inhibits transcription activity by p53 differently depending on concentrations. At the bottom of the graph is schematically shown the dosage of HDART. The ordinate of the graph represents the relative activity of luciferase expressed from Bax promoter.

FIG. 8 is a graphical representation showing the result of measurement of transcription inhibition by HDART. This result was obtained by using the GAL4 reporter analyzing system without p53 in order to see whether or not HDART directly acts on p300 to inhibit transcription. In the middle of this graph is shown the dosage of HDART. At the bottom of the graph is schematically shown the analyzing system. The Gal4-p300 fusion protein binds to the binding site of GAL4, thereby causing the luciferase gene as the reporter to express.

FIG. 9 is a photograph of electrophoresis showing the result of analysis to see the avidity between p300 and HDART by using GST-p300 fusion protein. It is noted that total proteins obtained by immunoprecipitation with anti GST antibody are detected by staining with Coomassie Blue. It is also noted that labeled HDART is detected by autoradiography.

FIG. 10 is a photograph showing the result of investigation to see if expression of intrinsic HDART is suppressed by western blotting.

FIG. 11 is a diagram showing the result of investigation to see the effect of HDART siRNA on the apoptosis which is induced after addition of etoposide.

FIG. 12 is a bar graph showing the average of the results obtained from the experiments (shown in FIG. 11) which were repeated twice.

BEST MODE FOR CARRYING OUT THE INVENTION

The invention will be described in more detail with reference to the following examples, which are not intended to restrict the scope thereof.

Example 1

Isolation of HDART cDNA

For identification of the human novel gene, an experiment was carried out to determine the base sequence of EST clone plasmid W52930 of ATCC (American Type Culture Collection) which had remained unanalyzed. The determined sequence suggested that the W52930 insert contains a nucleic acid which is involved in transcription control.

In order to determine the sequence of the 5' upstream region of ORF, the 5' RACE process was carried out according to 5' RACE System (Gibco BRIJ) and attached protocol by using primer JP3 AS1 (sequence No. 3) and JP3 AS2 (sequence No. 4) obtained from cell strain established by EB virus from normal human peripheral blood. Incidentally, in this example, the base sequence was determined by means of sequence reaction with BigDye Terminator Cycle Sequencing FS Ready Reaction Kit (from PE Biosystems Corp.) and also by means of electrophoresis and analysis with "ABI PRISM™ 310 Genetic Analyzer" (from PE Biosystems Corp.).

Figure 1A:
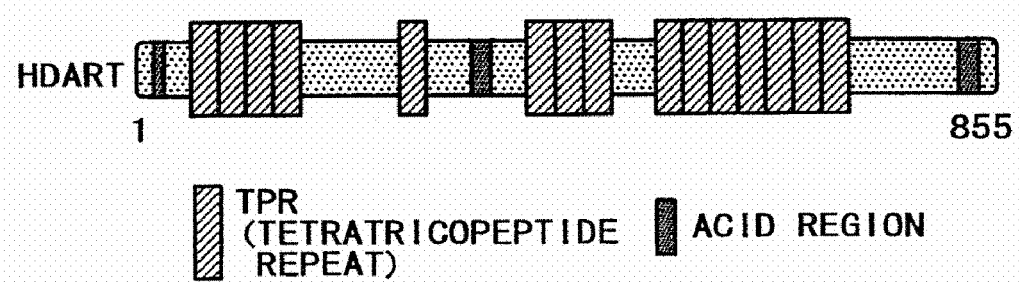
FIG. 1A is a schematic diagram showing the structure of HDART protein and FIG. 1B shows photographs showing the result of intracellular local analysis of HDART.

The entire cDNA sequence of HDART was identified by combining the base sequence determined in W52930 insert with the 5' upstream sequence obtained as mentioned above. The thus identified cDNA sequence is shown in sequence No. 1. Also, the amino acid sequence inferred from the cDNA sequence is shown in sequence No. 2. HDART codes 855 amino acids and possesses 15 TPR domains and 3 acid regions. (FIG. 1A) Incidentally, this protein is referred to a HDART.

Next, an antibody for HDART was prepared in order to analyze the intracellular localization of HDART. PCR was carried out by using the primer His-S1 (sequence No. 5) and His-AS1 (sequence No. 6), with the above-mentioned Plasmid W52930 being a template. With the PCR produce digested by BamHI and XhoI, the region of HDART coded with 296 to 431 amino acids was subcloned into BamHI and XhoI sites of pTrc HisB vector (Invitrogen). The recombinant protein of HDART (His tagged HDART protein) was introduced for expression into E. coli, strain BL21 (from Novagen Corp.) according to the attached protocol. The desired protein was purified by using Ni-NTA Spin Kit (QIAGEN) with Ni-NTA resin according to the attached protocol.

Figure 1B:
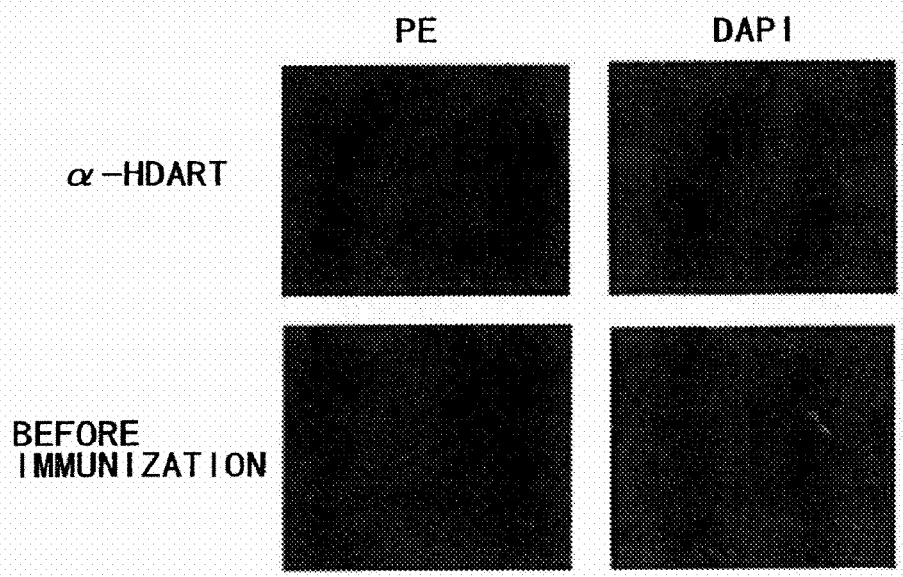

Using the thus purified protein (5 mg) as an antigen, an antihuman HDART. Rabbit antiserum was prepared in the usual way. This antiserum was further purified by using His-tagged HDART protein and ProtOn™ Kit (from Multiple Peptide System Corp.). In this way there was obtained an antihuman HDART polyclonal antibody. By using the thus obtained antibody, HeLa cells fixed on a chamber slide was immunostained. Immunostaining was performed in the same way as above by using, as the negative reference, a rabbit serum which is not yet immunized. Simultaneously with immunostaining, the nuclear DNA of the cell was stained with DAPI. The immunostaining and DAPI staining revealed that the nucleus was stained by the anti HDART antibody. (FIG. 1B)

Example 2

Suppression by HDART of p53-Dependent Transcriptional Activation

The following experiment was carried out in order to investigate whether or not the above-mentioned protein is involved in transcription. First, U-20S cells ($5 \times 10^4$ cells/well) derived from human osteosarcoma having wild p53 were sowed on a 24-well plate. After cultivation for 16 hours, pcDNA3-HDART expressing vector was introduced into the cells by using Effectene™ (from Qiagen Corp.), together with Bax promoter reporter plasmid (0.3 μg) as reporter plasmid and internal control phRL-TK plasmid (5 ng). The Bax promoter reporter plasmid is one in which firefly luciferase gene is spliced to the understream of the promoter sequence of Bax gene; thus transcription from Bax promoter is performed p53-dependently and luciferase as the reporter gene is expressed. In other words, by measuring the luciferase activity, it is possible to measure the activity of transcription of p53-dependent Bax promoter. The cDNA3-HDART vector was assembled by performing PCR using primer S3 (sequence No. 13) and AS8 (sequence No. 14), with W52930 being a template, and then splicing the PCR product (after digestion with BamHI) to pcDNA3 (Invitrogen Corp. California, USA) which had been obtained by digestion with BamHI. Incidentally, the amount of the expression vector introduced was 0, 0.2, and 0.5 μg, and correction was made with pcDNA plasmid so that the amount of total DNA introduced was 0.5 μg.

After introduction, cultivation was carried out at 37° C. in 5% carbon dioxide gas by using as a culture medium Dullbecco's modified Eagle medium (D-MEM) containing 10% fetal calf serum. After 24 hours, the cells were recovered by trypsin treatment, and they were tested for luciferase activity and *Renilla* luciferase activity by using Dual-Luciferase assay system (from Promega Corp.) according to the attached protocol. Lumat LB9501 (from Berthold Corp.) was used for measurement. Luciferase activity corrected by the value of *Renilla* luciferase activity was regarded as the transcription activity in order to average the efficiency of introduction of gene into individual wells. The same experiments with two identical samples were repeated twice, and the average and standard deviation of four results are shown in FIG. 2. Incidentally, the error bar denotes the standard deviation.

As shown in FIG. 2, HDART suppressed the activity of transcription from Bax promoter depending on the amount introduced. This result indicates that HDART suppresses the p53-dependent transcription activity.

Example 3

Suppression of Transcription Involving p53 by HDART of Various Promoters

It was found in Example 2 above that HDART suppresses transcription from Bax promoter which may have its transcription activated p53. Consequently, this example was designed to investigate the effect of HDART on p53 target gene promoter other than Bax mentioned above.

Into J-20S cells and HCT116 cells (derived from human colon carcinoma), both having wild p53, were transfected 0.3 μg of p21 promoter or pG13 reporter plasmid, 5 ng of phRL plasmid, and 0.5 μg of expression vector of pcDNA3(-) or pcDNA3-HDART(+) by using "Effectene" in the same way as mentioned above. Incidentally, it is considered that both p21 promoter and pG13 promoter have its transcription activated by p53 so that luciferase as reporter gene is expressed.

Figure 3:
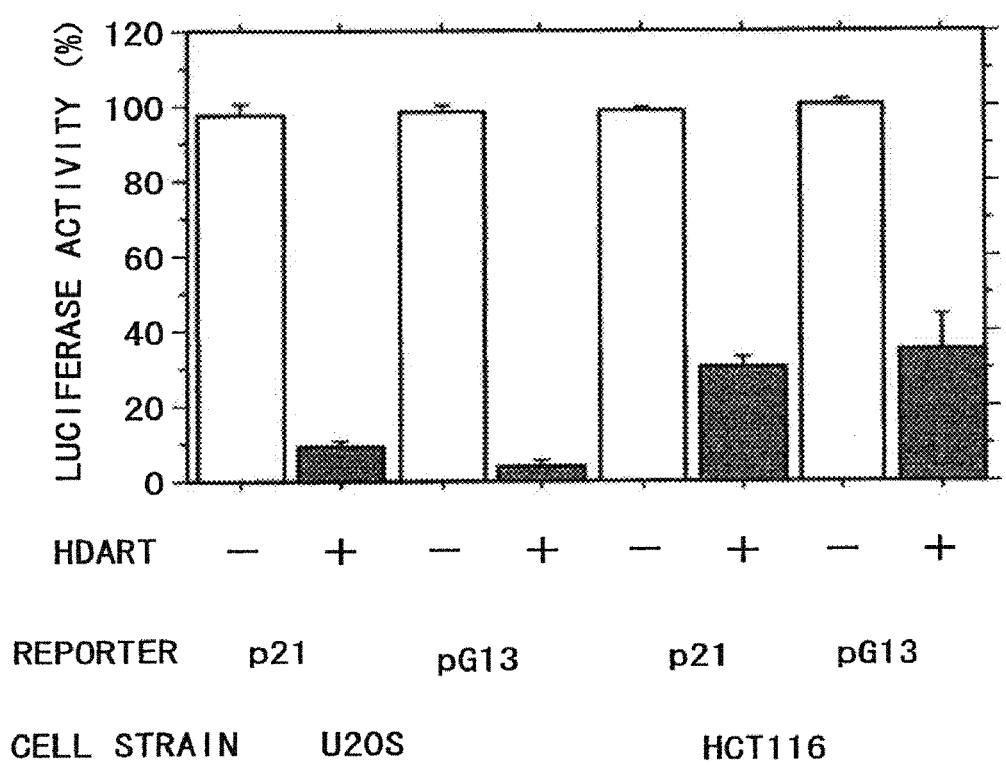
FIG. 3 is a graphical representation showing how much HDART suppresses the transcription of HDART in terms of luciferase activity connected to the downstream of promoter, in experiments with two kinds of cells (U2OS and HCT116 in which p53 is expressed) and two kinds of promoters (p21 and pG13 to which p53 binds, according to reports). In this figure, the mark "−" indicates that HDART was not administered and the mark "+" indicates that HDART was administered.

Twenty-four hours after introduction, luciferase activity and *Renilla* luciferase activity were measured in the same way as in Example 2. The value of luciferase activity was corrected by the value of *Renilla* luciferase activity. The luciferase value after correction in the case where pcDNA3 was introduced is regarded as 100%, and the average value for two experiments is shown in FIG. 3. The error bar denotes the standard deviation.

As shown in FIG. 3, HDART(-) activates transcription from p21 and pG13 promoters, whereas HDART(+) suppresses the activation of transcription from these promoters. This result suggests that HDART suppresses the activation of transcription by p53.

Example 4

Activity of HDART to Suppress the Activation of Transcription by Exogenous p53

In order to confirm the effect of HDART on suppressing the activation of transcription by p53, experiments were carried out in which exogenous p53 was introduced into cells and whether or not HDART suppresses the activation of transcription by p53 was examined in the following manner.

Figure 4:
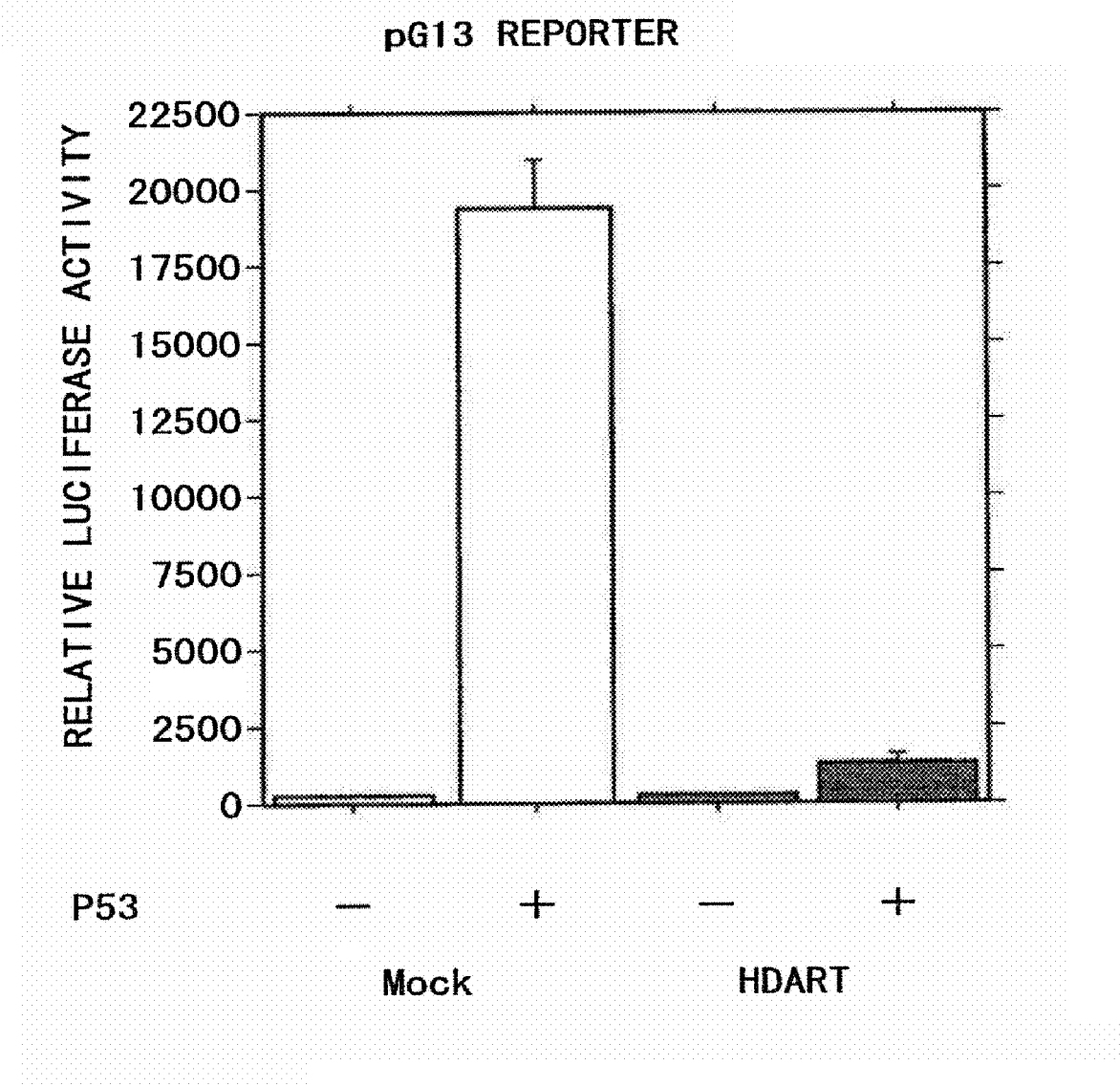
FIG. 4 is a graphical representation showing the result of measurement of the luciferase activity in pG13 reporter gene which is observed when p53 and HDART are artificially administered from the outside of the cell. In this figure, "Mock" denotes control cells without HDART administration, and "HDART" denotes cells with HDART administration. The mark "−" indicates that p53 was not administered and the mark "+" indicates that p53 was administered.

Into SaoS2 cells (p53 negative) derived from human osteosarcoma were transfected 0.2 μg of pG13 reporter plasmid, 5 ng of phRL, plasmid, 0.4 μg of pcDNA3(-) or pcDNA3-HA-p53(+), and 0.4 μg of pcDNA3(-) or pcDNA3-HDART(+) expression vector. Twenty-four hours after introduction, luciferase activity and *Renilla* luciferase activity were measured. The value of luciferase activity, with the transfection efficiency corrected by *Renilla* luciferase activity, was measured twice, and the average value is shown in FIG. 4. The error bar denotes the standard deviation.

As shown in FIG. 4, in the cells (Mock) with no HDART introduced therein, the introduction of p53 greatly activates transcription in pG13 reporter. However, in the cells with HDART introduced therein, the activation of transcription by p53 was suppressed to almost the same level as negative cells with no p53 introduced therein. This result clearly indicates that HDART suppresses the activation of transcription by p53.

Example 5

Suppression by HDART of the Induction of Gadd45 and p21 Gene Expression by p53 after Stimulation with Irradiation Irradiation on cells induces p53, and the thus induced p53 induces the expression of target gene Gadd45 and p21 (Cip1/Waf1). The following experiments were conducted to see whether or not HDART suppresses the activation of transcription by the intrinsic p53 which is induced by irradiation.

Into U-20S cells was transfected 1 μg of pcDNA3(-) or pcDNA3-HDART(+) expression vector. Twenty-four hours after introduction, irradiation (12 Gy) was carried out. The negative reference was prepared in the same way as above without irradiation. Four hours after irradiation, mRNA was purified from these cells. RT-PCR was carried out using the primers of p21, GADD45, and β-Actin as shown below.

```
p21 sense primer:
                                           (sequence No. 7)
GGA AGC TTC CTG CCG AAG TCA GTT CCT TGT GGA p21 antisense primer:
                                           (sequence No. 8)
CCA AGC TTC CTG TGG GCG GAT TAG GGC TT GADD45 sense primer:
                                           (sequence No. 9)
ATG GAT AAG GTG GGG GAT GC GADD45 antisense primer:
                                          (sequence No. 10)
TGA TCC ATG TAG CGA CTT TC β-Actin sense primer:
                                          (sequence No. 11)
GAC CTG ACA GAC TAC CTC AT β-Actin antisense primer:
                                          (sequence No. 12)
AGA CAG CAC TGT GTT GGC AT
```

The products obtained by PCR with these primers in combination were detected by electrophoresis. (FIG. 5) The expression of HDART and the increase of p53 protein in the cells were confirmed by Western blotting that employs the anti HDART antibody or anti p53 antibody mentioned above. The Western blotting was carried out in the way known to those skilled in the art.

Figure 5:
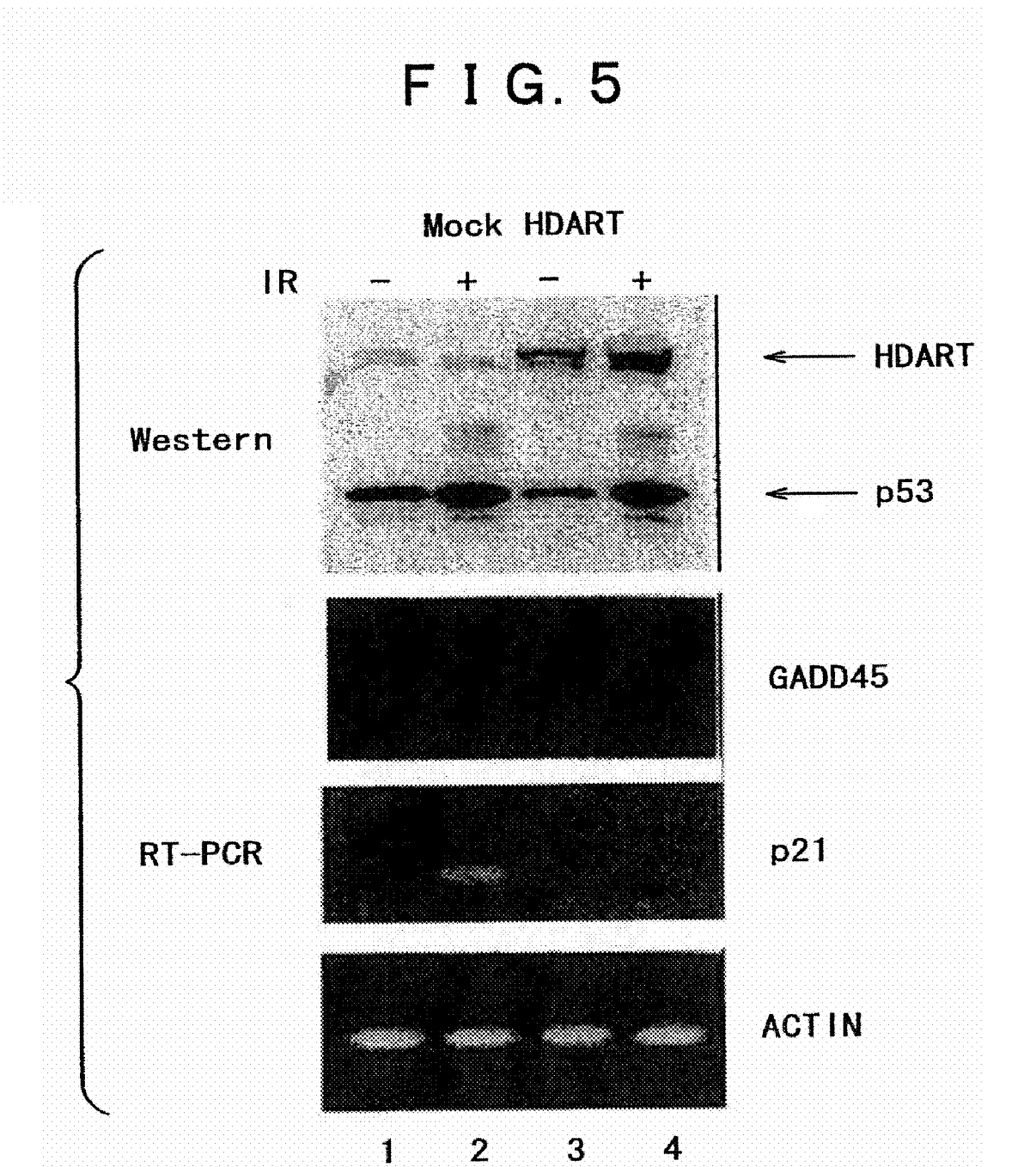
FIG. 5 is a photograph of electrophoresis showing the results of analysis by RT-PCR of the expression of p53 target gene, which was observed when the intrinsic p53 was induced by irradiation with ionizing radiation (IR) and then HDART was administered. In this figure, the mark "−" indicates that irradiation was not performed, and the mark "+" indicates that irradiation was performed. Gadd45 and p21 are p53 target genes to be analyzed and actin is an internal control.

As shown in FIG. 5, it was confirmed that p53 is expressed with increased band strength in irradiated cells more than in unirradiated cells. In the absence of HDART, the expression of target gene p21 and GADD45 was induced (lane 2) in correspondence to the expression and induction of p53. By contrast, in the presence of HDART, the expression of target gene p21 and GADD45 corresponding to the expression and induction of p53 was suppressed (lane 4). This result indicates that HDART suppresses the expression and induction of target gene that depend on the intrinsic p53 under physiological conditions.

Example 6

Inhibition by HDART of the Discontinuance of p53-Dependent Cell Cycle after Irradiation In view of the observation that p53 suppresses the activation of p53-dependent transcription, experiments were conducted as follows to investigate how this suppression affects the bioactivity of p53. The bioactivity of p53 is the effect on the discontinuance of cell cycle.

Into U-20S cells was introduced 2 μg of an expression vector of pcDNA3 (Mock) or pcDNA3-HDART (HDART). Sixteen hours after introduction, the cells were irradiated with ionizing radiation (12 Gy) and the control cells were not irradiated (0 Gy). Twenty-four hours after irradiation, the cells were fixed with 70% ethanol and the DNA was stained with PI (Propidium iodide). Then, the cell cycle was analyzed by using a flow cytometer.

Figure 6:
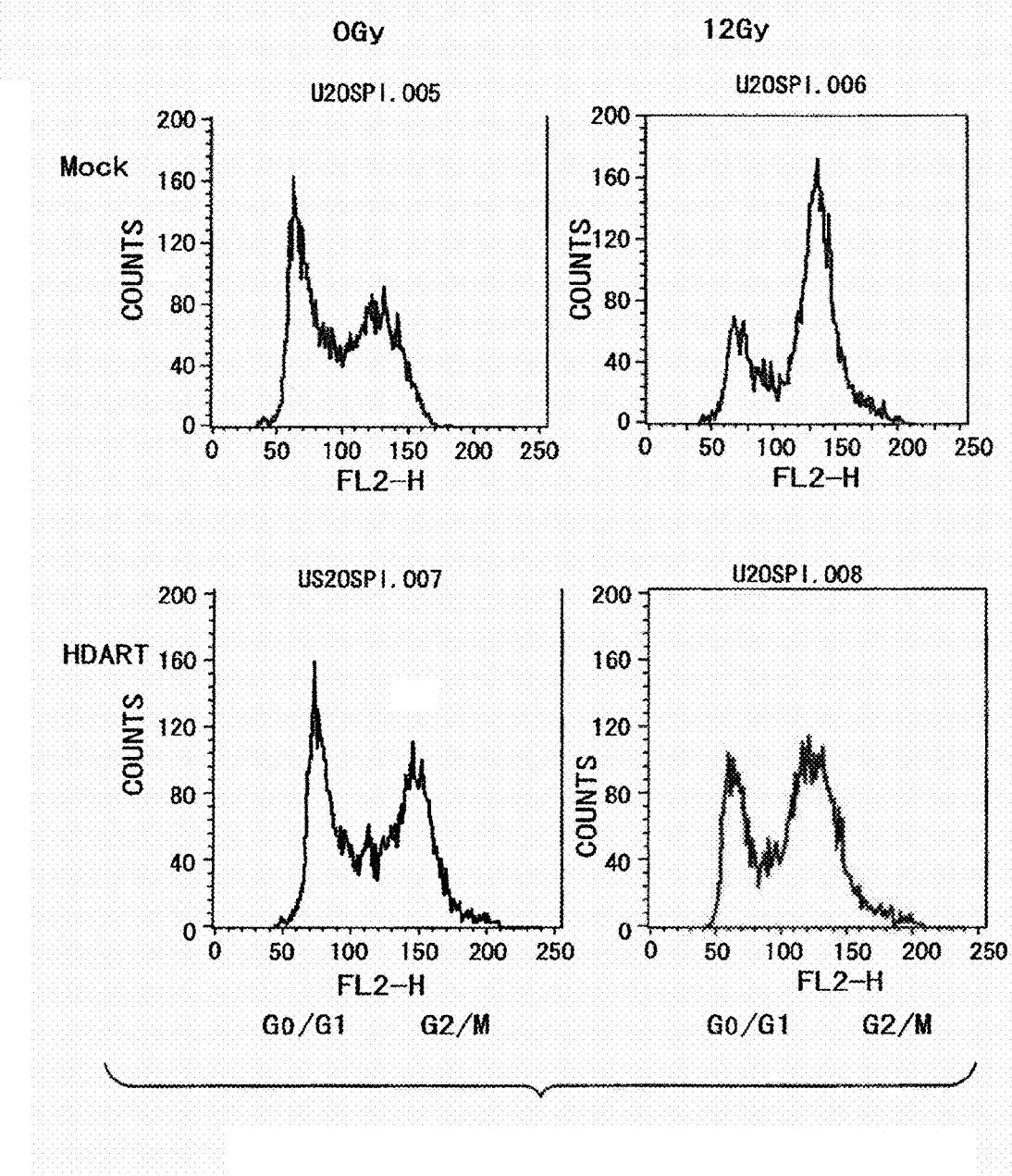
FIG. 6 is a histogram of flow cytometry showing the result of analysis to see whether or not administration of HDART inhibits the discontinuation of p53-dependent cell cycle which is caused by irradiation of ionizing radiation. It is noted that irradiation brings about the discontinuation of cell cycle (right up) and administration of HDART after irradiation eliminates the discontinuation of cell cycle (right down).

The analysis of cell cycle gave the result shown in FIG. 6. It is noted that the irradiated sample with no HDART introduced exhibits a higher G2/M peak than the unirradiated sample with no HDART introduced which suggests that the cell cycle stops at the G2/M. By contrast, it is also noted that the irradiated sample with HDART introduced exhibits the inhibition of G2/M arrest by irradiation (12 Gy). Thus it was demonstrated that HDART suppresses the bioactivity of p53 through the suppression of transcriptional activation.

Example 7

Suppression by HDART of Transcriptional Activation by Coactivator p300 of p53

It is considered that the transcriptional activation of various genes by p53 is caused by binding to p53 of p300 as a coactivator. With thin in mind, experiments were conducted as follows to investigate whether HDART inhibits the transcriptional activation of p53 due to its direct action on p53 or due to its action on the coactivator p300.

Into U-20S cells were introduced 20 ng of p21 promoter reporter plasmid, 5 ng of phRL plasmid, 0.5 μg of expression vector of pcDNA3(−) or pcDNA3-HDART, and 0.3 μg of expression vector of pCMV(−) or pCMV-p300(+). Twenty-four hours after introduction, the luciferase activity and Renilla luciferase activity were measured. The efficiency of introduction was corrected by Renilla luciferase, and the luciferase activation value was obtained. This luciferase activation value is shown here in terms of an average value of two measurements. The value of the cells with no p300 and HDART introduced (with pCMV(−) and pcDNA3(−) introduced) is assigned to 100%, and the values of other samples are given in terms of relative luciferase activity. (FIG. 7) The error bar denotes the standard deviation.

Figure 7:
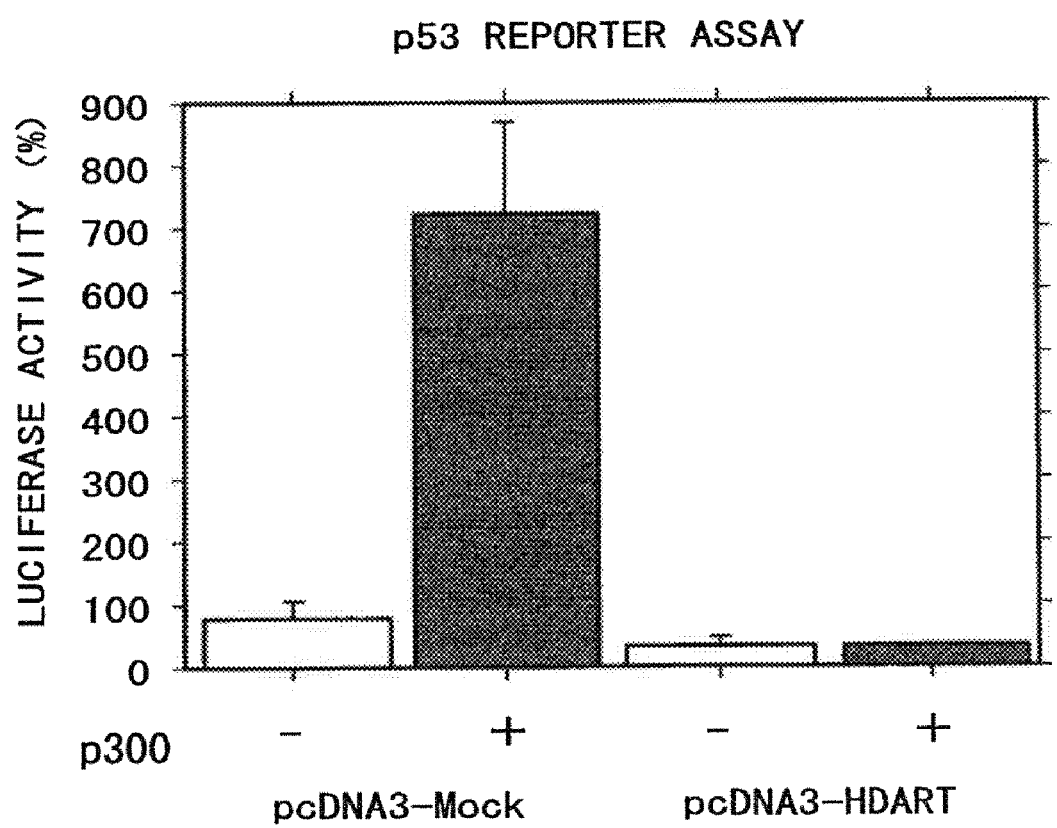
FIG. 7 is a graph showing the result of analysis to see if HDART inhibits the transcription activity of coactivator p300 of p53. In this graph, the mark "+" denotes those cells to which p300 gene was introduced from the outside for excessive expression, and the mark "−" denotes those cells to which p300 gene was not introduced from the outside. "pDNA3-mock" represents the control group to which plasmid without HDART was administered and "pDNA3-HDART" represents the group to which plasmid with HDART was administered.

As shown in FIG. 7, in the absence of HDART, the transcriptional activation by p53 greatly increases through expression of p300. By contrast, in the presence of HDART, the transcriptional activation by p300 is completely suppressed. Moreover, the results indicate that the transcriptional activation by p53 is also suppressed in the presence of HDART.

Example 8

Concentration-Dependent Suppression by HDART of Transcriptional Activation of p300

Experiments were carried out to investigate how the effect of HDART on the transcriptional activation by p300 changes as its concentration changes.

Into U-20S cells were introduced 0.1 μg of GAL4 reporter plasmid, 5 ng of phRL plasmid, 0.1 μg of pcDNA3-GAL4p300 plasmid, and the expression vector of pcDNA3-HDART in varied amounts (0, 0.1, 0.3, and 0.5 μg). The total amount of expression vector was adjusted to 0.5 μg with pcDNA3 plasmid. Twenty-four hours after introduction, the luciferase activity and Renilla luciferase activity were measured. The luciferase activation value, with the efficiency of introduction corrected, is given in terms of an average of two measurements. The value in the case of pcDNA3 alone is assigned to 100%. (FIG. 8) The error bar denotes the standard deviation.

As shown in FIG. 8, HDART suppresses more the induction of expression of luciferase gene by p300 as its amount increases. This result shows that HDART suppresses the ability of transcriptional activation possessed by p300 itself.

Example 9

Direct Binding of HDART and p300 Protein

The foregoing Examples 7 and 8 demonstrated that HDART inhibits the transcriptional activation by p300. So, experiments were carried out as follows to investigate whether or not the inhibition of p300 by HDART is due to direct binding to each other. Samples used for binding are purified GST-p300 fusion protein and HDART protein synthesized in vitro.

Into *E. coli* DH5 α strain (TOYOBO) was introduced according to the attached protocol each of fusion protein expression vector of GST (glutathione-S-transferase), GST-p300 ΔCH1 (p300 cysteine/histidine-rich region 1:300 to 528 residues of amino acid sequence of p300), and GST-p300 ΔCH1 (p300 cysteine/histidine-rich region 1:1700 to 1966 residues of amino acid sequence of p300). After introduction, the bacteria were cultured for expression at 37° C. for 4 hours in the presence of 0.1 mM of IPTG.

The bacteria were collected and bacteriolyzed with GST Lysis buffer (50 mM Tris-HCl, pH 8.5, 300 mM LiCl, 0.5% NP40, 5 mM EDTA, 1 mM PMSF). The cells of the bacteria were ultrasonically homogenized for extraction of protein. GST or GST fusion protein was obtained by purification with glutathione Sepharose 4B beads (from Amersham Pharmacia Corp.)

On the other hand, HDART protein was synthesized from 2 μg of pcDNA3-HDART plasmid by using the in vitro translation system (TNT® from Promega Corp.). It was labeled with $^{35}$S-methionine (AG1094, from Amersham Pharmacia Corp.).

To 1 ml of GST Lysis buffer were added 1 μg of purified GST or GST fusion protein mentioned above, 10 μl of labeled HDART protein, and 30 μl of glutathione Sepharose 4B beads. After mixing, the resulting mixture was kept at 4° C. for 1 hour for reaction. After reaction, the Sepharose was rinsed four times with GST Lysis buffer. The protein was eluted by heating at 98° C. for 5 minutes with a sample buffer (60 mM Tris-HCl, pH 8.4, 10% SDS, 50% Glycerol, and 25% 2-Mercaptoethanol). The eluate was separated by SDS polyacrylamide gel electrophoresis. The gel which had undergone electrophoresis was stained with Coomassie Blue solution. The separated protein was identified (FIG. 9 upper part) and then dried. Subsequently, the labeled HDART was detected by autoradiography (FIG. 9 lower part).

As FIG. 9 shows, it turned out that HDART does not bind to GST protein alone (lane 2) but binds to CH1 and CH3 domains of p300 (lanes 3 and 5). It also turned out that HDART hardly binds to ΔCH1 which is the CH1 domain of p300 from which the cysteine/histidine-rich domain is deleted (lane 4). The foregoing demonstrates that the binding of HDART to p300 needs the cysteine/histidine-rich domain on p300.

Example 10

Increase in Transcriptional Activity of p53 (or Enhancement of Apoptosis) by siRNA Knockdown Effect of Intrinsic HDART The importance of HDART in the ordinary bioactivity of p53 was investigated by observing the effect on the bioactivity of p53 which is produced when the expression of intrinsic HDART is suppressed.

Such technique as antisense RNA and ribozyme RNA have been used to suppress the gene expression at cell levels. It has recently been shown that it is possible to efficiently and specifically suppress the gene expression by using siRNA (small interfering RNA). (Elbashir S M., Harborth J., Lendeckel W., Yalcin A., Weber K., Tuschl T., Elbashier S M. et al., Nature 2001, May 24; 411 (6836): 494-8) The present inventors conducted experiments to investigate the effect on the induction of apoptosis after DNA double strand break as one of the major functions of p53, which is produced when the expression of intrinsic HDART is suppressed by using siRNA specific to HDART. It is anticipated that suppressing the expression of HDART which is a p53 inhibiting molecule leads to activation of p53 and enhancement of apoptosis. Etopside was used as an inducer for DNA double strand break. This agent is one of anticancer agents used for remedy of testis and bladder carcinoma, lung cancer, malignant lymphoma, and acute leukemia. It inhibits topoisomerase II alpha and brings about DNA double strand break for cells at the cell cycle of S phase and G2/M phase, thereby inducing apoptosis. (Ogawa I. et al., "Gan to kagaku chiryou hou (Cancer and its chemical therapy)", 10, 2403 (1983), Noda K. et al., "Gan to kagaku chiryou hou (Cancer and its chemical therapy)", 21, 1633 (1994)) It is said that p53 is essential for the induction of apoptosis. (Lowe, S. W., Ruley, H. E., Jacks, T., & Housman, D. E. (1993). Cell 74, 954-967, Lowe, S. W., Bodis, S., McClatchey, A., Remington, L., Ruley, H. E., Fisher, D., Housman, D. E., & Jacks, T. (1994). Science 266, 807810, Fan, S. J., Eldeiry, W. S., Bae, I., Freeman, J., Jondle, D., Bhatia, K., Fornace, A. J., Magrath, I., Kohn, K. W., & OÅf-Connor, P. M. (1994). Cancer Res. 54, 58245830, Fujiwara, T., Grimm, E. A., Mukhopadhyay, T., Zhang, W. W., Owenschaub, L. B., & Roth, J. A. (1994). Cancer Res. 54, 22872291). Therefore, if the effect on apoptosis induced by etoposide is investigated, it is possible to elucidate the relation between the major bioactivity of p53 (or the induction of apoptosis) and the function of HDART. However, this agent affects the growth of normal cells, causing side effect such as leukopenia and alopecia. It also causes secondary leukemia that occurs several years after administration. The clinical application of siRNA is expected if it suppresses the expression of HDART and increases in sensitivity to etoposide.

(1) Design of siRNA

With the target being 5'-AACCAATTCTCTGT-CAAATGC/sequence No. 15 (corresponding to the 93 to 111th bases counting from A of the first methionine) in mRNA of HDART, siRNA was prepared from 5'-CCAAUU-CUCUGUCAAAUGCTT/sequence No. 16 as sense strand and 5'-GCAUUUGACAGAGAAUUGGTT/sequence No. 17, RNA-DNA hybrid oligo sequence as antisense strand. siRNA for luciferace (GL3 gene) was prepared from 5'-CU-UACGCUGAGUACUUCGATT/sequence No. 18 as sense strand and 5'-UCGAAGUACUCAGCGUAAGTT/sequence No. 19, RNA-DNA hybrid oligo sequence as antisense strand, according to literature cited from Elbashir et al. (Elbashir S M., Harborth J., Lendeckel W., Yalcin A., Weber K., Tuschl T., Elbashier S M., et al., Nature 2001 May 24; 411 (6836): 494-8) All of them were synthesized by Japan Bio Services Co., Ltd. (JbioS) upon request.

(2) Preparation of siRNA

The thus synthesized sense strand and antisense strand in the form of RNA-DNA hybrid oligo sequence were diluted to 50 μM. The resulting solutions, 30 μl each, were mixed with 15 μl of 5× annealing buffer (50 mM Tris-HCl, 250 mM KCl, 7.5 mM $MgCl_2$). The mixed solution was heated at 90° C. for 1 minute and allowed to stand at 37° C. for 60 minutes after spin down. There was obtained 20 μM siRNA.

(3) Introduction of siRNA into Cells and Analysis of Apoptosis $5 \times 10^5$ cells were sowed on a 6-cm plate. After culture for 16 hours, they were transfected with 10 μl of 20 μM siRNA by using OligofectAMINE (from Invitrogen Corp.) according to the attached protocol. After culture for 48 hours that followed introduction of siRNA, the cells were given 10 μM of etoposide. (The cells for control were not given etoposide.) After additional culture for 48 hours, the cells were examined for the ratio of apoptosis by using FACSCalibur (from Becton Dickinson Corp.) after staining recovered cells (unfixed cells) with 25 μg/ml of propidium iodide (PI). The strongly PI positive fraction was regarded as dead cells.

(4) Results of Experiments (a) Into U-20S cells (derived from human osteosarcoma) and H1299 cells (derived from human colon cancer) was introduced HDART siRNA to see whether or not it suppresses the expression of intrinsic HDART. Introduction of siRNA was accomplished by the above-mentioned method. After 48 hours, the cells were recovered, and the expression of proteins was examined by using anti HDART antibody and anti α-tubulin antibody in the usual way according to Western blotting. The results are shown in FIG. 10. Lanes 1 and 2 and lanes 3 and 4 respectively represent the proteins extracted from U-20S cells and H1299 cells. Also, lanes 1 and 3 represent the protein into which was introduced siRNA (Cont. siRNA) for luciferace of internal control, and lanes 2 and 4 represent the protein into which was introduced siRNA (HDART siRNA) for HDART. Lanes 2 and 4 suggest a decrease in the expression of HDART protein. No variation was observed among samples in the expression of α-tubulin of control protein.

(b) The next experiment was conducted to investigate the effect of HDART siRNA on apoptosis induced after addition of etoposide. The results are shown in FIG. 11. The upper two diagrams represent the samples with Cont. siRNA, and the lower two diagrams represent the samples with HDART siRNA. The left two diagrams represent the samples without etoposide, and the right two diagrams represent the samples with etoposide. In each diagram, the X-axis represents the fluorescence intensity of PI and the Y-axis represents the number of cells. The portion indicated by a bar represents the strongly PI-positive fraction of dead cells. The percentage represents the ratio of cells in the portion indicated by the bar.

(c) The experiment mentioned in (b) above was repeated twice. The results in terms of average are shown in FIG. 12 (bar chart), in which the error bar represents the standard deviation. The significance level for *1 and *2 is P<5% according to Student's t-test. They were regarded as significant. It was found that the sample with HDART siRNA is about twice as high as the control sample in apoptosis induced by etoposide.

This example demonstrated that siRNA for HDART suppress the expression of intrinsic HDART very efficiently and that suppressing the expression of intrinsic HDART by siRNA for HDART enhances the sensitivity to etoposide as an anticancer agent. If a system is realized which permits HDART siRNA to express in vivo efficiently, it would be possible to reduce the dosage of anticancer agent owing to enhancement of sensitivity, thereby reducing side effect. Moreover, it would be possible to increase the sensitivity for cancers for which the conventional anticancer agent is not effective at the optimum concentration.

INDUSTRIAL APPLICABILITY

HDART of the present invention binds to p300, thereby inhibiting transcription by transcription factor involved with p300 as coactivator. p300 is an important protein which participates in various transcription factors and causes the expression of various bioactivities. The inhibitor for such an important protein is useful for the study of functions of p300.

HDART inhibits p300 and consequently inhibits the discontinuance of cell cycle that depends on the transcription factor p53. This suggests that HDART would inhibit the expression of p53 functions through p300 inhibition, thereby inducing transformation. It is expected that HDART would be useful for the development of therapeutic drugs for diseases involved with p300 or p53 functional anomaly.

The result of investigations on the physiological effect that is produced by knock-down of HDART by siRNA shows the enhancement of apoptosis by increased transcriptional activation of p300 and p53. Therefore, the inhibitor of HDART is of great use as an anticancer agent or a concomitant drug for anticancer agents (that increases sensitivity to anticancer agents).

The invention claimed is:

1. An isolated nucleic acid comprising Sequence No. 1.

2. A composition for inhibition of transcription which contains an isolated nucleic acid according to claim 1.

3. A recombinant vector comprising a nucleic acid according to claim 1.

4. The recombinant vector of claim 3, which is an expression vector.

5. A host cell comprising the recombinant vector of claim 4.

* * * * *